US012559549B2

(12) United States Patent
Choi

(10) Patent No.: US 12,559,549 B2
(45) Date of Patent: Feb. 24, 2026

(54) ANTIBODY BINDING TO SUPER-REPRESSOR IκB (SRIκB) OR ANTIGEN BINDING FRAGMENT THEREOF

(71) Applicant: ILIAS BIOLOGICS, INCORPORATED, Daejeon (KR)

(72) Inventor: Chul Hee Choi, Daejeon (KR)

(73) Assignee: ILIAS BIOLOGICS, INCORPORATED, Daejeon (KR)

( * ) Notice: Subject to any disclaimer, the term of this patent is extended or adjusted under 35 U.S.C. 154(b) by 854 days.

(21) Appl. No.: 17/789,946

(22) PCT Filed: Dec. 31, 2020

(86) PCT No.: PCT/KR2020/019486
§ 371 (c)(1),
(2) Date: Jun. 29, 2022

(87) PCT Pub. No.: WO2021/137655
PCT Pub. Date: Jul. 8, 2021

(65) Prior Publication Data
US 2022/0389086 A1     Dec. 8, 2022

(30) Foreign Application Priority Data
Dec. 31, 2019     (KR) ........................ 10-2019-0179381

(51) Int. Cl.
| | |
|---|---|
| *A61K 39/395* | (2006.01) |
| *A61K 39/00* | (2006.01) |
| *C07K 16/00* | (2006.01) |
| *C07K 16/18* | (2006.01) |
| *C12N 15/62* | (2006.01) |
| *C12N 15/85* | (2006.01) |
| *A61P 25/00* | (2006.01) |
| *A61P 25/28* | (2006.01) |
| *A61P 29/00* | (2006.01) |

(52) U.S. Cl.
CPC .............. *C07K 16/18* (2013.01); *A61K 39/00* (2013.01); *A61K 39/395* (2013.01); *A61K 39/39541* (2013.01); *A61K 39/3955* (2013.01); *C07K 16/00* (2013.01); *C12N 15/62* (2013.01); *C12N 15/85* (2013.01); *A61K 2039/505* (2013.01); *A61P 25/00* (2018.01); *A61P 25/28* (2018.01); *A61P 29/00* (2018.01)

(58) Field of Classification Search
CPC .......... A61K 2039/505; A61K 38/1709; C07K 16/18; C07K 16/00; A61P 29/00; A61P 25/28; A61P 19/02; A61P 37/00; A61P 25/00; A61P 37/06; G01N 2800/56; G01N 33/5023; G01N 33/74; G01N 2800/52; C12N 15/62; C12N 15/85
See application file for complete search history.

(56) References Cited

FOREIGN PATENT DOCUMENTS

| | | | | |
|---|---|---|---|---|
| WO | WO-2019118906 A2 * | 6/2019 | ........... | A61K 49/001 |
| WO | WO-2021137655 A1 * | 7/2021 | ............. | C07K 16/18 |
| WO | WO-2022005117 A1 * | 1/2022 | ............. | A61K 39/00 |

OTHER PUBLICATIONS

MacCallum et al., J. Mol. Biol., 1996; 262: 732-745.*
Pascalis et al., The Journal of Immunology, 2002; 169: 3076-3084.*
Casset et al., BBRC, 2003; 307: 198-205.*
Vajdos et al., J. Mol. Biol. 2002; 320: 415-428.*
Holm et al., Mol. Immunol., 2007; 44: 1075-1084.*
Chen et al., J. Mol. Bio., 1999; 293: 865-881.*
Wu et al., J. Mol. Biol., 1999; 294:151-162.*
Burgess et al. J of Cell Bio. 1990, 111:2129-2138.*
Bowie et al. Science, 1990, 247:1306-1310.*
Pawson et al. 2003, Science 300:445-452.*
Alaoui-Ismaili et al., Cytokine Growth Factor Rev. 2009; 20:501-507.*
Guo et al., PNAS 2004; 101:9205-9210.*
Rudikoff et al., Proc. Natl. Acad. Sci. USA 1982 vol. 79: p. 1979.*

* cited by examiner

*Primary Examiner* — Chang-Yu Wang
(74) *Attorney, Agent, or Firm* — Morgan, Lewis & Bockius LLP

(57) ABSTRACT

Provided are a monoclonal or polyclonal antibody against srIκB or an antigen-binding fragment thereof, a nucleic acid encoding the same, a vector including the nucleic acid, a host cell into which the nucleic acid or the vector is introduced, a method of preparing the antibody or the antigen-binding fragment thereof, and use thereof. The antibody specifically binding to srIκB or the antigen-binding fragment thereof according to the present disclosure is characterized by binding to srIκB, in particular, mutation sites with high affinity, as compared to the wild-type IκB. Accordingly, the antibody specifically binding to srIκB or the antigen-binding fragment thereof according to the present disclosure may be usefully applied to industrial fields where srIκB is used as a target protein.

8 Claims, 10 Drawing Sheets
Specification includes a Sequence Listing.

[FIG. 1]

[FIG. 4]
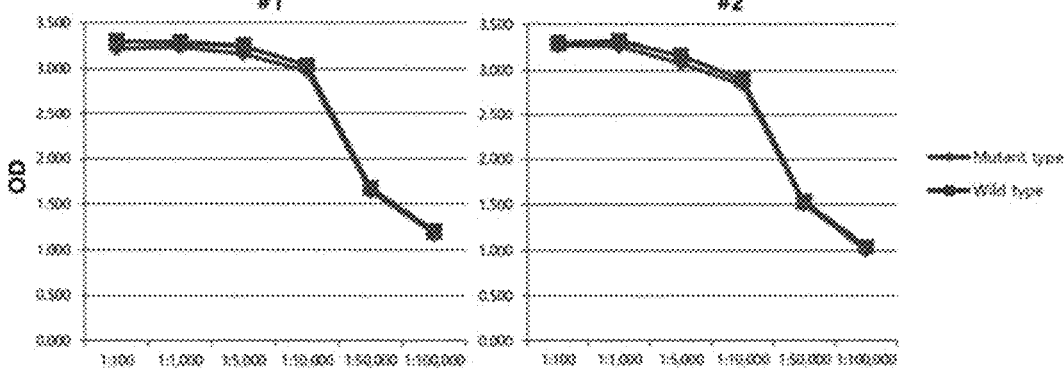
| Sample | Dilution factor | SrikB | | | |
|---|---|---|---|---|---|
| | | #1 | | #2 | |
| | | Mutant type | Wild type | Mutant type | Wild type |
| Pre-serum | 1:100 | 0.248 | 0.231 | 0.294 | 0.306 |
| Test serum | 1:100 | 3.222 | 3.291 | 3.275 | 3.282 |
| | 1:1,000 | 3.241 | 3.285 | 3.285 | 3.318 |
| | 1:5,000 | 3.162 | 3.245 | 3.078 | 3.159 |
| | 1:10,000 | 2.973 | 3.037 | 2.841 | 2.897 |
| | 1:50,000 | 1.832 | 1.676 | 1.497 | 1.524 |
| | 1:100,000 | 1.173 | 1.194 | 1.006 | 1.041 |
[FIG. 5]
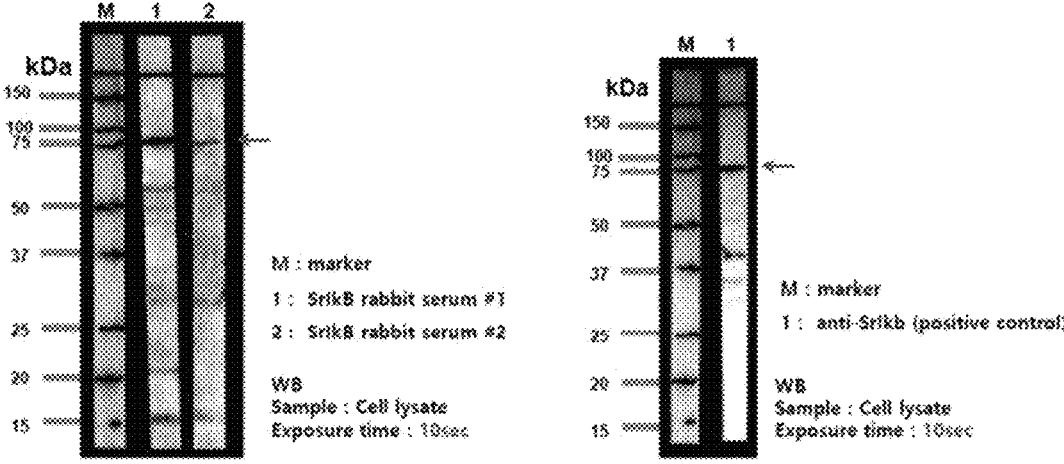

[FIG. 6]
[ MANI protocol ]
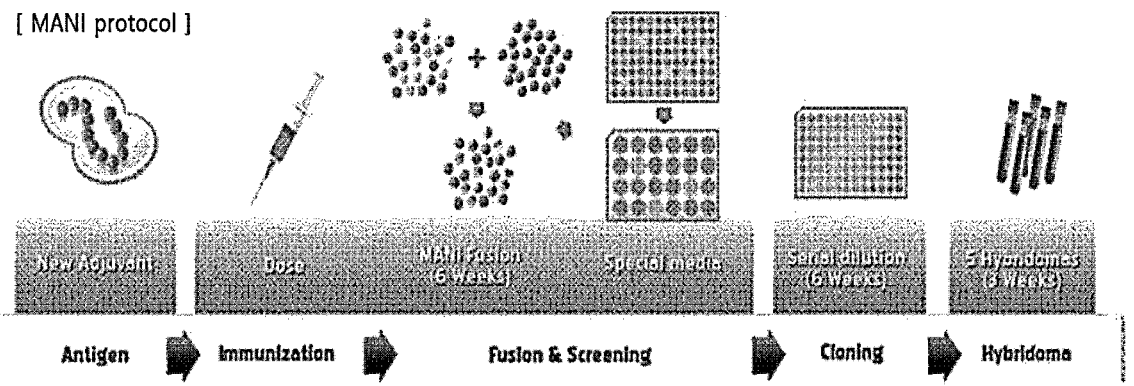
Antigen ➡ Immunization ➡ Fusion & Screening ➡ Cloning ➡ Hybridoma
[FIG. 7]
Workflow
• *In vivo* production
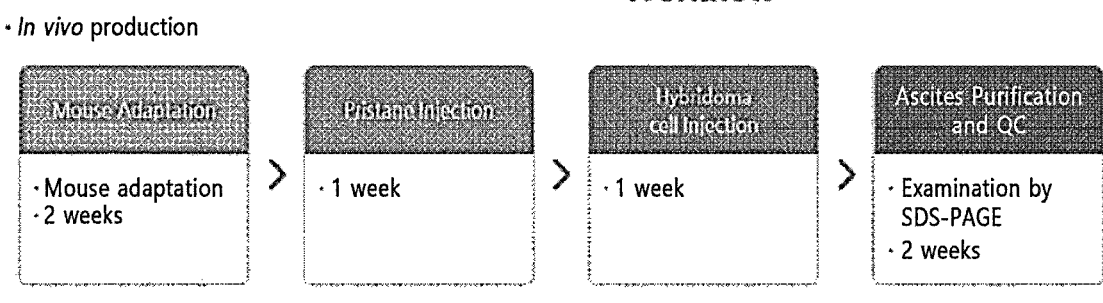
| Mouse Adaptation | Pristane Injection | Hybridoma cell Injection | Ascites Purification and QC |
|---|---|---|---|
| • Mouse adaptation<br>• 2 weeks | • 1 week | • 1 week | • Examination by SDS-PAGE<br>• 2 weeks |

[FIG. 8]
| Clone No. | srkB mutant peptide (Ag) | srkB WT peptide | Lysate | SMCC control |
|---|---|---|---|---|
| 2D8 | 1.841 | 1.196 | 0.061 | 1.383 |
| 3E12 | 0.067 | 0.037 | 0.041 | 0.106 |
| 3F8 | 1.898 | 1.896 | 0.048 | 0.103 |
| 3F12 | 0.063 | 0.039 | 0.039 | 0.108 |
| 3G5 | 0.096 | 0.048 | 0.087 | 0.109 |
| 3G7 | 0.196 | 0.185 | 0.037 | 0.101 |
| 4A12 | 0.063 | 0.043 | 0.039 | 0.114 |
| 4B12 | 0.075 | 0.054 | 0.052 | 0.115 |
| 4D8 | 0.068 | 0.048 | 0.057 | 0.123 |
| 5A2 | 1.887 | 1.748 | 0.047 | 0.112 |
| 5A5 | 0.058 | 0.043 | 0.043 | 0.122 |
| 5A9 | 0.060 | 0.040 | 0.050 | 0.108 |
| 5C4 | 0.057 | 0.042 | 0.051 | 0.135 |
| 5C5 | 0.058 | 0.041 | 0.046 | 0.107 |
| 5E8 | 0.116 | 0.062 | 0.038 | 0.112 |
| 5A6 | 0.073 | 0.056 | 0.053 | 0.120 |
| 6B5 | 0.728 | 0.681 | 0.056 | 0.099 |
| 6C10 | 1.398 | 0.047 | 0.053 | 0.118 |
| 6C13 | 0.056 | 0.039 | 0.044 | 0.116 |
| 6F3 | 0.073 | 0.041 | 0.061 | 0.107 |
| 7A12 | 0.116 | 0.071 | 0.062 | 0.183 |
| 7B12 | 0.097 | 0.063 | 0.067 | 0.166 |
| 7H3 | 0.418 | 0.232 | 0.075 | 0.628 |
| Clone No. | srkB mutant peptide (Ag) | srkB WT peptide | Lysate | SMCC control |
|---|---|---|---|---|
| 8A9 | 0.102 | 0.083 | 0.065 | 0.172 |
| 8B11 | 0.107 | 0.054 | 0.063 | 0.183 |
| 9C9 | 0.111 | 0.081 | 0.046 | 0.172 |
| 9C10 | 0.331 | 0.201 | 0.046 | 0.195 |
| 9F6 | 0.133 | 0.079 | 0.067 | 0.196 |
| 9H8 | 2.737 | 0.071 | 0.070 | 0.384 |
| 9H9 | 0.079 | 0.083 | 0.053 | 0.176 |
| 10A1 | 0.070 | 0.061 | 0.055 | 0.187 |
| 10A3 | 0.074 | 0.083 | 0.056 | 0.178 |
| 10A4 | 0.081 | 0.054 | 0.061 | 0.171 |
| 10B1 | 0.071 | 0.053 | 0.057 | 0.197 |
| 10C1 | 0.081 | 0.069 | 0.069 | 0.176 |
| 10H1 | 0.100 | 0.080 | 0.082 | 1.878 |
| 10C1 | 0.079 | 0.061 | 0.066 | 0.171 |
| 10H1 | 2.392 | 1.813 | 0.107 | 2.421 |
| negative | 0.044 | 0.035 | 0.055 | 0.086 |
| positive | 1.491 | 1.368 | 0.068 | 1.334 |
[FIG. 9]
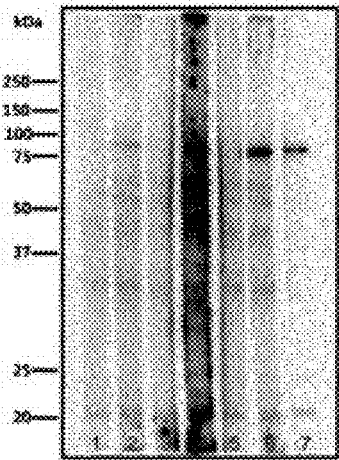
| 1 | 2 | 3 | 4 | 5 | 6 | 7 |
|---|---|---|---|---|---|---|
| 2F8 | 5A2 | 6B5 | 6C10 | 9E10 | 9H8 | Positive |

[FIG. 10]
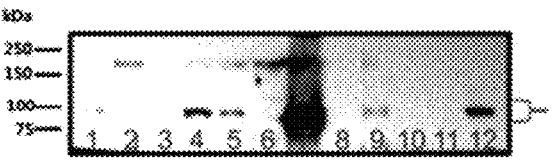
| 1 | 2 | 3 | 4 | 5 | 6 | 7 | 8 | 9 | 10 | 11 | 12 |
|---|---|---|---|---|---|---|---|---|----|----|----|
| 2F8 | 5A2 | 6B5 | 6C10 | 9H8 | 9E10 | Positive control | MS IgG | Serum #2 | Resin only | Clearing resin | IP Ag |
[FIG. 11]
| Clone No. | OD SrIkB (Ag) |
|-----------|---------------|
| 2F8 | 2.964 |
| 5A2 | 3.238 |
| 6C10 | 3.181 |
| 9H8 | 3.867 |

[FIG. 12]

|         | 2F8   | 5A2   | 6C10  | 9H8   |
|---------|-------|-------|-------|-------|
| IgG1    | 1.479 | 0.057 | 0.134 | 0.060 |
| IgG2a   | 0.103 | 0.058 | 1.861 | 1.173 |
| IgG2b   | 0.054 | 1.418 | 0.077 | 0.046 |
| IgG3    | 0.057 | 0.066 | 0.071 | 0.132 |
| IgA     | 0.051 | 0.050 | 0.055 | 0.062 |
| IgM     | 0.051 | 0.051 | 0.051 | 0.091 |
| Kappa   | 0.898 | 0.828 | 0.695 | 0.898 |
| Lambda  | 0.046 | 0.048 | 0.078 | 0.045 |

[FIG. 13]
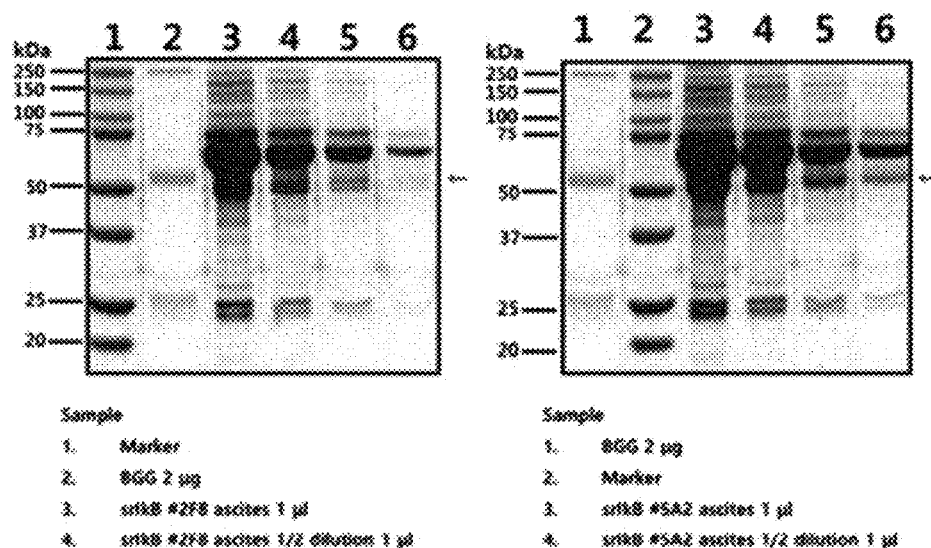
| Sample | | Sample | |
| --- | --- | --- | --- |
| 1. | Marker | 1. | 8GG 2 μg |
| 2. | 8GG 2 μg | 2. | Marker |
| 3. | srlk8 #2F8 ascites 1 μl | 3. | srlk8 #5A2 ascites 1 μl |
| 4. | srlk8 #2F8 ascites 1/2 dilution 1 μl | 4. | srlk8 #5A2 ascites 1/2 dilution 1 μl |
| 5. | srlk8 #2F8 ascites 1/4 dilution 1 μl | 5. | srlk8 #5A2 ascites 1/4 dilution 1 μl |
| 6. | srlk8 #2F8 ascites 1/8 dilution 1 μl | 6. | srlk8 #5A2 ascites 1/8 dilution 1 μl |
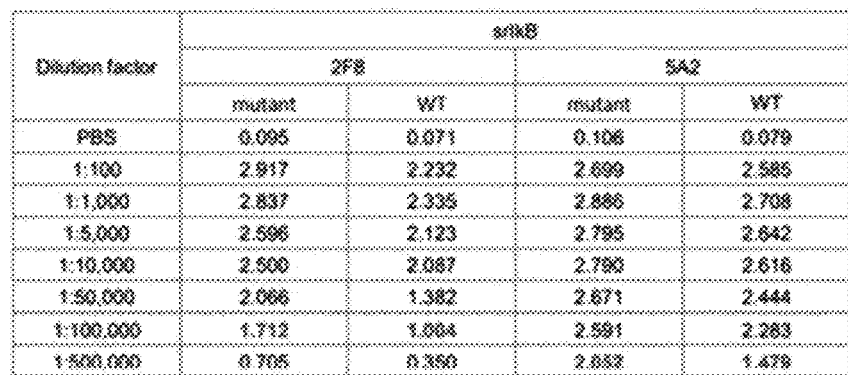
| | srlk8 | | | |
| --- | --- | --- | --- | --- |
| Dilution factor | 2F8 | | 5A2 | |
| | mutant | WT | mutant | WT |
| PBS | 0.095 | 0.071 | 0.106 | 0.079 |
| 1:100 | 2.917 | 2.232 | 2.699 | 2.585 |
| 1:1,000 | 2.837 | 2.335 | 2.886 | 2.708 |
| 1:5,000 | 2.596 | 2.123 | 2.795 | 2.642 |
| 1:10,000 | 2.500 | 2.087 | 2.790 | 2.616 |
| 1:50,000 | 2.066 | 1.382 | 2.671 | 2.444 |
| 1:100,000 | 1.712 | 1.004 | 2.591 | 2.283 |
| 1:500,000 | 0.706 | 0.360 | 2.033 | 1.479 |
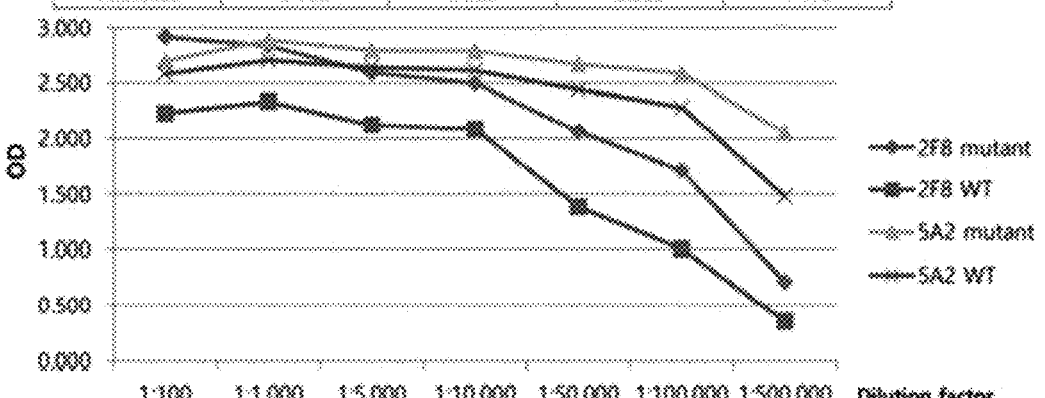

[FIG. 14]
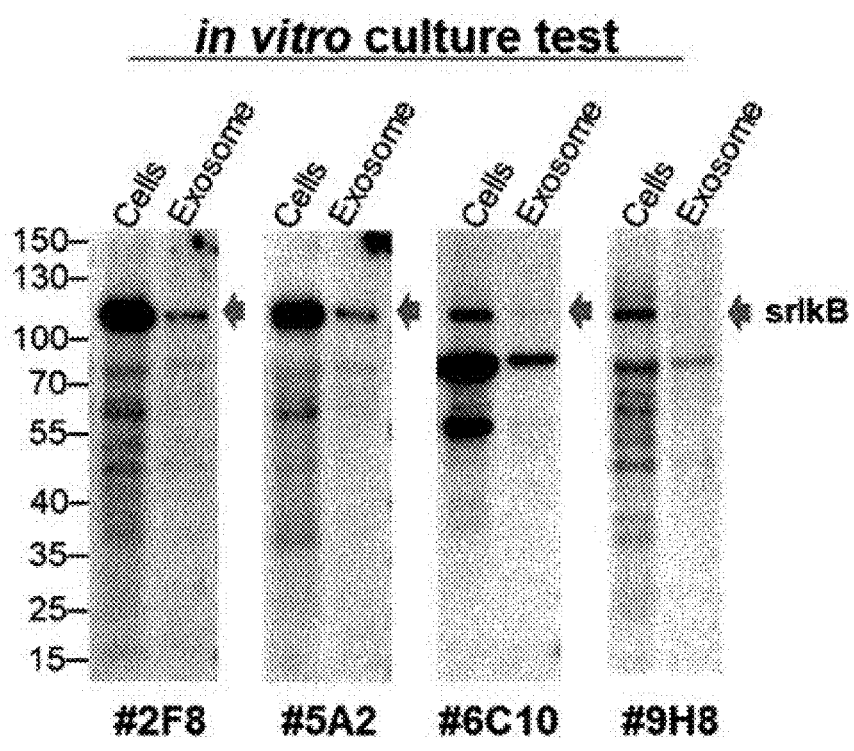

[FIG. 15]
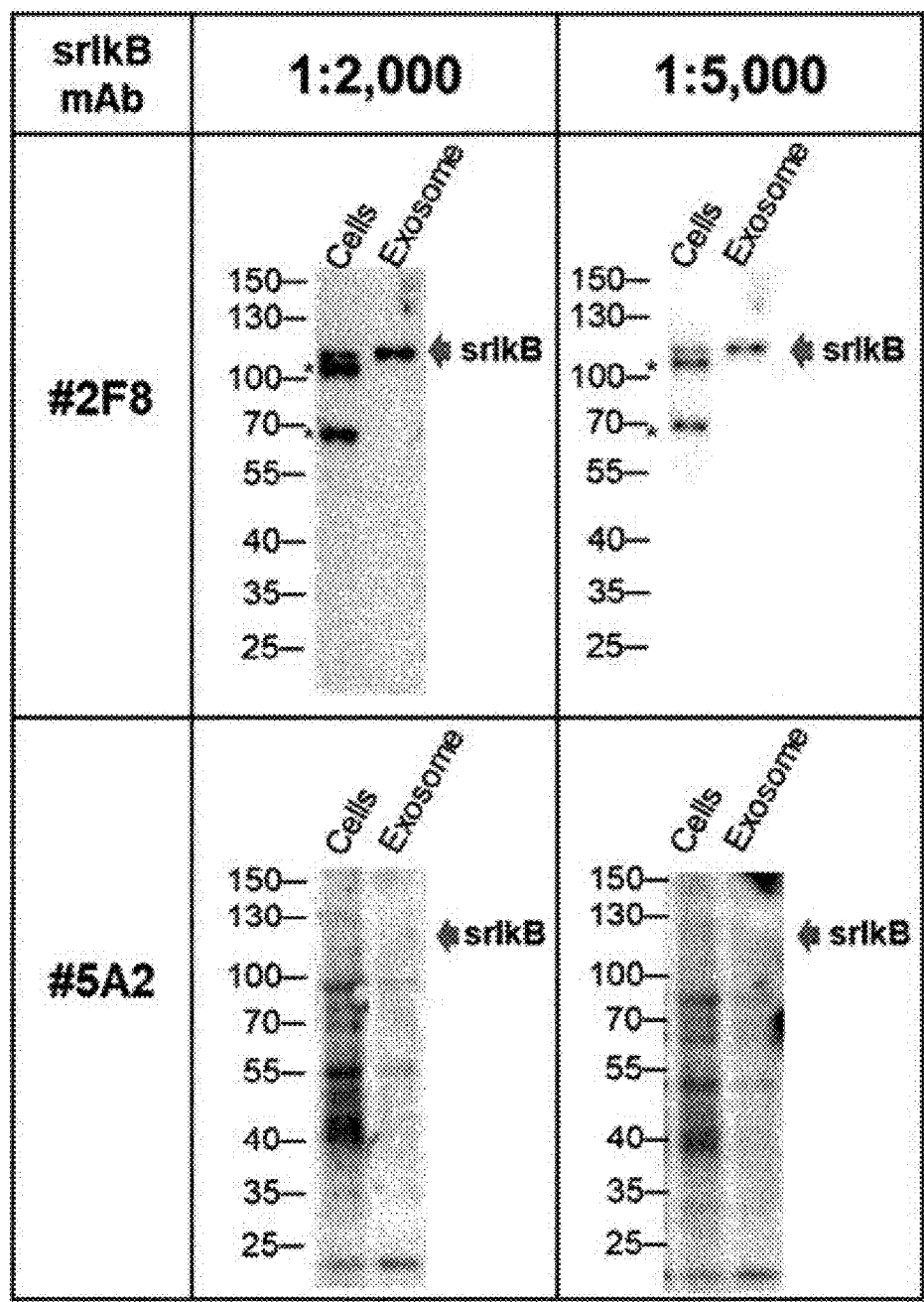
*; non-specific band

SEQUENCE LISTING

```
<160> NUMBER OF SEQ ID NOS: 76

<210> SEQ ID NO 1
<211> LENGTH: 13
<212> TYPE: PRT
<213> ORGANISM: Artificial Sequence
<220> FEATURE:
<223> OTHER INFORMATION: Synthetic construct

<400> SEQUENCE: 1

Asp Arg His Asp Ser Gly Leu Asp Ser Met Lys Asp Glu
1               5                   10
```

```
<210> SEQ ID NO 2
<211> LENGTH: 13
<212> TYPE: PRT
<213> ORGANISM: Artificial Sequence
<220> FEATURE:
<223> OTHER INFORMATION: Synthetic construct

<400> SEQUENCE: 2

Asp Arg His Asp Ala Gly Leu Asp Ala Met Lys Asp Glu
1               5                   10

<210> SEQ ID NO 3
<211> LENGTH: 5
<212> TYPE: PRT
<213> ORGANISM: Artificial Sequence
<220> FEATURE:
<223> OTHER INFORMATION: Synthetic construct

<400> SEQUENCE: 3

Gly Tyr Ser Met Ser
1               5

<210> SEQ ID NO 4
<211> LENGTH: 17
<212> TYPE: PRT
<213> ORGANISM: Artificial Sequence
<220> FEATURE:
<223> OTHER INFORMATION: Synthetic construct

<400> SEQUENCE: 4

Tyr Ile Ser Ser Tyr Tyr Tyr Ser Thr Tyr Tyr Ala Asp Ser Val Lys
1               5                   10                  15

Gly

<210> SEQ ID NO 5
<211> LENGTH: 9
<212> TYPE: PRT
<213> ORGANISM: Artificial Sequence
<220> FEATURE:
<223> OTHER INFORMATION: Synthetic construct

<400> SEQUENCE: 5

Tyr Gly Tyr Ser Gly Tyr Phe Asp Tyr
1               5

<210> SEQ ID NO 6
<211> LENGTH: 15
<212> TYPE: PRT
<213> ORGANISM: Artificial Sequence
<220> FEATURE:
<223> OTHER INFORMATION: Synthetic construct

<400> SEQUENCE: 6

Arg Ala Ser Lys Ser Val Ser Thr Ser Gly Tyr Ser Tyr Met His
1               5                   10                  15

<210> SEQ ID NO 7
<211> LENGTH: 7
<212> TYPE: PRT
<213> ORGANISM: Artificial Sequence
<220> FEATURE:
<223> OTHER INFORMATION: Synthetic construct

<400> SEQUENCE: 7

Leu Val Ser Asn Leu Glu Ser
```

-continued

```
1               5

<210> SEQ ID NO 8
<211> LENGTH: 7
<212> TYPE: PRT
<213> ORGANISM: Artificial Sequence
<220> FEATURE:
<223> OTHER INFORMATION: Synthetic construct

<400> SEQUENCE: 8

Gln His Ile Arg Glu Leu Thr
1               5

<210> SEQ ID NO 9
<211> LENGTH: 118
<212> TYPE: PRT
<213> ORGANISM: Artificial Sequence
<220> FEATURE:
<223> OTHER INFORMATION: Synthetic construct

<400> SEQUENCE: 9

Glu Val Gln Val Val Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Ser Met Ser Trp Val Arg Gln Ala Pro Gly Lys Gly Leu Glu Trp Val
        35                  40                  45

Ser Tyr Ile Ser Ser Tyr Tyr Tyr Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Gly Tyr Ser Gly Tyr Phe Asp Tyr Trp Gly Gln Gly Thr
            100                 105                 110

Pro Val Thr Val Ser Ala
        115

<210> SEQ ID NO 10
<211> LENGTH: 118
<212> TYPE: PRT
<213> ORGANISM: Artificial Sequence
<220> FEATURE:
<223> OTHER INFORMATION: Synthetic construct

<400> SEQUENCE: 10

Glu Val Gln Arg Val Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Ser Met Ser Trp Val Arg Gln Ala Pro Gly Lys Gly Leu Glu Trp Val
        35                  40                  45

Ser Tyr Ile Ser Ser Tyr Tyr Tyr Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Gly Tyr Ser Gly Tyr Phe Asp Tyr Trp Gly Gln Gly Thr
            100                 105                 110
```

```
Pro Val Thr Val Ser Ser
        115

<210> SEQ ID NO 11
<211> LENGTH: 118
<212> TYPE: PRT
<213> ORGANISM: Artificial Sequence
<220> FEATURE:
<223> OTHER INFORMATION: Synthetic construct

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Ser Met Ser Trp Val Arg Gln Ala Pro Gly Lys Gly Leu Glu Trp Val
            35                  40                  45

Ser Tyr Ile Ser Ser Tyr Tyr Tyr Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Gly Tyr Ser Gly Tyr Phe Asp Tyr Trp Gly Gln Gly Thr
            100                 105                 110

Leu Val Thr Val Ser Ser
        115

<210> SEQ ID NO 12
<211> LENGTH: 118
<212> TYPE: PRT
<213> ORGANISM: Artificial Sequence
<220> FEATURE:
<223> OTHER INFORMATION: Synthetic construct

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Ser Met Ser Trp Val Arg Gln Ala Pro Gly Lys Gly Leu Glu Trp Val
            35                  40                  45

Ser Tyr Ile Ser Ser Tyr Tyr Tyr Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Gly Tyr Ser Gly Tyr Phe Asp Tyr Trp Gly Gln Gly Thr
            100                 105                 110

Pro Val Thr Val Ser Ser
        115

<210> SEQ ID NO 13
<211> LENGTH: 118
<212> TYPE: PRT
<213> ORGANISM: Artificial Sequence
<220> FEATURE:
<223> OTHER INFORMATION: Synthetic construct
```

<400> SEQUENCE: 13

Glu Val Gln Val Val Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Ser Met Ser Trp Val Arg Gln Ala Pro Gly Lys Gly Leu Glu Trp Val
        35                  40                  45

Ser Tyr Ile Ser Ser Tyr Tyr Tyr Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Gly Tyr Ser Gly Tyr Phe Asp Tyr Trp Gly Gln Gly Thr
            100                 105                 110

Thr Val Thr Val Ser Ser
        115

<210> SEQ ID NO 14
<211> LENGTH: 118
<212> TYPE: PRT
<213> ORGANISM: Artificial Sequence
<220> FEATURE:
<223> OTHER INFORMATION: Synthetic construct

<400> SEQUENCE: 14

Glu Val Gln Val Val Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Ser Met Ser Trp Val Arg Gln Ala Pro Gly Lys Gly Leu Glu Trp Val
        35                  40                  45

Ser Tyr Ile Ser Ser Tyr Tyr Tyr Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Gly Tyr Ser Gly Tyr Phe Asp Tyr Trp Gly Gln Gly Thr
            100                 105                 110

Thr Val Thr Val Ser Ser
        115

<210> SEQ ID NO 15
<211> LENGTH: 123
<212> TYPE: PRT
<213> ORGANISM: Artificial Sequence
<220> FEATURE:
<223> OTHER INFORMATION: Synthetic construct

<400> SEQUENCE: 15

Asp Val Leu Met Thr Gln Thr Pro Ala Ser Leu Ala Val Ser Leu Gly
1               5                   10                  15

Gln Arg Ala Thr Ile Ser Tyr Arg Ala Ser Lys Ser Val Ser Thr Ser
            20                  25                  30

Gly Tyr Ser Tyr Met His Trp Asn Gln Gln Lys Pro Gly Gln Pro Pro
        35                  40                  45

-continued

```
Arg Leu Leu Ile Tyr Leu Val Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ile Arg
                85                  90                  95

Glu Leu Thr Arg Ser Glu Gly Gly Pro Ser Trp Ser Gly Ala Tyr Thr
            100                 105                 110

Phe Gly Gly Gly Thr Lys Leu Glu Leu Lys Arg
        115                 120
```

```
<210> SEQ ID NO 16
<211> LENGTH: 123
<212> TYPE: PRT
<213> ORGANISM: Artificial Sequence
<220> FEATURE:
<223> OTHER INFORMATION: Synthetic construct

<400> SEQUENCE: 16
```

```
Asp Ile Gln Met Thr Gln Ser Pro Ala Ser Leu Ala Val Ser Leu Gly
1               5                   10                  15

Gln Arg Ala Thr Ile Ser Tyr Arg Ala Ser Lys Ser Val Ser Thr Ser
                20                  25                  30

Gly Tyr Ser Tyr Met His Trp Asn Gln Gln Lys Pro Gly Gln Pro Pro
        35                  40                  45

Arg Leu Leu Ile Tyr Leu Val Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ile Arg
                85                  90                  95

Glu Leu Thr Arg Ser Glu Gly Gly Pro Ser Trp Ser Gly Ala Tyr Thr
            100                 105                 110

Phe Gly Gly Gly Thr Lys Leu Glu Leu Lys Arg
        115                 120
```

```
<210> SEQ ID NO 17
<211> LENGTH: 123
<212> TYPE: PRT
<213> ORGANISM: Artificial Sequence
<220> FEATURE:
<223> OTHER INFORMATION: Synthetic construct

<400> SEQUENCE: 17
```

```
Asp Ile Gln Met Thr Gln Ser Pro Ala Ser Leu Ala Val Ser Leu Gly
1               5                   10                  15

Gln Arg Ala Thr Ile Ser Tyr Arg Ala Ser Lys Ser Val Ser Thr Ser
                20                  25                  30

Gly Tyr Ser Tyr Met His Trp Asn Gln Gln Lys Pro Gly Gln Pro Pro
        35                  40                  45

Arg Leu Leu Ile Tyr Leu Val Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ile Arg
                85                  90                  95

Glu Leu Thr Arg Ser Glu Gly Gly Pro Ser Trp Ser Gly Ala Tyr Thr
```

-continued
```
                    100                 105                 110

Phe Gly Gly Gly Thr Lys Leu Glu Leu Lys Arg
        115                 120

<210> SEQ ID NO 18
<211> LENGTH: 123
<212> TYPE: PRT
<213> ORGANISM: Artificial Sequence
<220> FEATURE:
<223> OTHER INFORMATION: Synthetic construct

<400> SEQUENCE: 18

Asp Ile Lys Met Thr Gln Ser Pro Ala Ser Leu Ala Val Ser Leu Gly
1               5                   10                  15

Gln Arg Ala Thr Ile Ser Tyr Arg Ala Ser Lys Ser Val Ser Thr Ser
            20                  25                  30

Gly Tyr Ser Tyr Met His Trp Asn Gln Gln Lys Pro Gly Gln Pro Pro
        35                  40                  45

Arg Leu Leu Ile Tyr Leu Val Ser Asn Leu Glu Pro Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ile Arg
                85                  90                  95

Glu Leu Thr Arg Ser Glu Gly Gly Gln Ser Trp Lys Gly Ala Tyr Thr
                100                 105                 110

Phe Gly Gly Gly Thr Lys Leu Glu Ile Lys Arg
        115                 120

<210> SEQ ID NO 19
<211> LENGTH: 118
<212> TYPE: PRT
<213> ORGANISM: Artificial Sequence
<220> FEATURE:
<223> OTHER INFORMATION: Synthetic construct

<400> SEQUENCE: 19

Asp Ile Val Met Thr Gln Ser Pro Ala Ser Leu Ala Val Ser Leu Gly
1               5                   10                  15

Gln Arg Ala Thr Ile Ser Tyr Arg Ala Ser Lys Ser Val Ser Thr Ser
            20                  25                  30

Gly Tyr Ser Tyr Met His Trp Asn Gln Gln Lys Pro Gly Gln Pro Pro
        35                  40                  45

Arg Leu Leu Ile Tyr Leu Val Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ile Arg
                85                  90                  95

Glu Leu Thr Arg Ser Glu Gly Gly Pro Ser Gly Ala Tyr Thr Phe Gly
                100                 105                 110

Gly Gly Thr Lys Leu Lys
        115

<210> SEQ ID NO 20
<211> LENGTH: 123
<212> TYPE: PRT
<213> ORGANISM: Artificial Sequence
<220> FEATURE:
```

<223> OTHER INFORMATION: Synthetic construct

<400> SEQUENCE: 20

```
Asp Ile Gln Met Thr Gln Ser Pro Ala Ser Leu Ala Val Ser Leu Gly
1               5                   10                  15

Gln Arg Ala Thr Ile Ser Tyr Arg Ala Ser Lys Ser Val Ser Thr Ser
            20                  25                  30

Gly Tyr Ser Tyr Met His Trp Asn Gln Gln Lys Pro Gly Gln Pro Pro
        35                  40                  45

Arg Leu Leu Ile Tyr Leu Val Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ile Arg
                85                  90                  95

Glu Leu Thr Arg Ser Glu Gly Gly Pro Ser Trp Ser Gly Ala Tyr Thr
            100                 105                 110

Phe Gly Gly Gly Thr Lys Leu Glu Leu Lys Arg
        115                 120
```

<210> SEQ ID NO 21
<211> LENGTH: 123
<212> TYPE: PRT
<213> ORGANISM: Artificial Sequence
<220> FEATURE:
<223> OTHER INFORMATION: Synthetic construct

<400> SEQUENCE: 21

```
Asp Ile Lys Met Asn Gln Ser Pro Ala Ser Leu Ala Val Ser Leu Gly
1               5                   10                  15

Gln Arg Ala Thr Ile Ser Tyr Arg Ala Ser Lys Ser Val Ser Thr Ser
            20                  25                  30

Gly Tyr Ser Tyr Met His Trp Asn Gln Gln Lys Pro Gly Gln Pro Pro
        35                  40                  45

Arg Leu Leu Ile Tyr Leu Val Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ile Arg
                85                  90                  95

Glu Leu Thr Arg Ser Glu Gly Gly Pro Ser Trp Ser Gly Ala Tyr Thr
            100                 105                 110

Phe Gly Gly Gly Thr Lys Leu Glu Leu Lys Arg
        115                 120
```

<210> SEQ ID NO 22
<211> LENGTH: 120
<212> TYPE: PRT
<213> ORGANISM: Artificial Sequence
<220> FEATURE:
<223> OTHER INFORMATION: Synthetic construct

<400> SEQUENCE: 22

```
Asp Ile Val Met Thr Gln Ala Pro Ala Ser Leu Ala Val Ser Leu Gly
1               5                   10                  15

Gln Arg Ala Thr Ile Ser Tyr Arg Ala Ser Lys Ser Val Ser Thr Ser
            20                  25                  30

Gly Tyr Ser Tyr Met His Trp Asn Gln Gln Lys Pro Gly Gln Pro Pro
```

-continued

```
              35                  40                  45
Arg Leu Leu Ile Tyr Leu Val Ser Asn Leu Glu Ser Gly Val Pro Ala
    50                  55                  60
Arg Phe Ser Gly Ser Gly Ser Gly Thr Asp Phe Thr Leu Asn Ile His
65                  70                  75                  80
Pro Val Glu Glu Glu Asp Ala Ala Thr Tyr Tyr Cys Gln His Ile Arg
                85                  90                  95
Glu Leu Thr Arg Ser Glu Gly Gly Pro Ser Trp Thr Gly Ala Tyr Thr
                100                 105                 110
Phe Gly Gly Gly Thr Lys Leu Asp
        115                 120

<210> SEQ ID NO 23
<211> LENGTH: 123
<212> TYPE: PRT
<213> ORGANISM: Artificial Sequence
<220> FEATURE:
<223> OTHER INFORMATION: Synthetic construct

<400> SEQUENCE: 23

Asp Ile Val Met Thr Gln Ser Pro Ala Ser Leu Ala Val Ser Leu Gly
1                   5                   10                  15
Gln Arg Ala Thr Ile Ser Tyr Arg Ala Ser Lys Ser Val Ser Thr Ser
                20                  25                  30
Gly Tyr Ser Tyr Met His Trp Asn Gln Gln Lys Pro Gly Gln Pro Pro
        35                  40                  45
Arg Leu Leu Ile Tyr Leu Val Ser Asn Leu Glu Ser Gly Val Pro Ala
    50                  55                  60
Arg Phe Ser Gly Ser Gly Ser Gly Thr Asp Phe Thr Leu Asn Ile His
65                  70                  75                  80
Pro Val Glu Glu Glu Asp Ala Ala Thr Tyr Tyr Cys Gln His Ile Arg
                85                  90                  95
Glu Leu Thr Arg Ser Glu Gly Gly Pro Ser Trp Ser Gly Ala Tyr Thr
                100                 105                 110
Phe Gly Gly Gly Thr Lys Leu Glu Leu Lys Arg
        115                 120

<210> SEQ ID NO 24
<211> LENGTH: 126
<212> TYPE: PRT
<213> ORGANISM: Artificial Sequence
<220> FEATURE:
<223> OTHER INFORMATION: Synthetic construct

<400> SEQUENCE: 24

Asp Ile Gln Met Thr Gln Ser Pro Ala Ser Leu Ala Val Ser Leu Gly
1                   5                   10                  15
Gln Arg Ala Thr Ile Ser Tyr Arg Ala Ser Lys Ser Val Ser Thr Ser
                20                  25                  30
Gly Tyr Ser Tyr Met His Trp Asn Gln Gln Lys Pro Gly Gln Pro Pro
        35                  40                  45
Arg Leu Leu Ile Tyr Leu Val Ser Asn Leu Glu Ser Gly Val Pro Ala
    50                  55                  60
Arg Phe Ser Gly Ser Gly Ser Gly Thr Asp Phe Thr Leu Asn Ile His
65                  70                  75                  80
Pro Val Glu Glu Glu Asp Ala Ala Thr Tyr Tyr Cys Gln His Ile Arg
                85                  90                  95
```

-continued

```
Glu Leu Thr Arg Ser Glu Gly Thr Lys Leu Glu Gly Ala Tyr Thr Phe
            100                 105                 110

Gly Gly Asp Gln Ala Gly Ala Glu Thr Asn Gly Cys Thr Ile
        115                 120                 125

<210> SEQ ID NO 25
<211> LENGTH: 123
<212> TYPE: PRT
<213> ORGANISM: Artificial Sequence
<220> FEATURE:
<223> OTHER INFORMATION: Synthetic construct

<400> SEQUENCE: 25

Asp Ile Val Leu Thr Gln Ser Pro Ala Ser Leu Ala Val Ser Leu Gly
1               5                   10                  15

Gln Arg Ala Thr Ile Ser Tyr Arg Ala Ser Lys Ser Val Ser Thr Ser
            20                  25                  30

Gly Tyr Ser Tyr Met His Trp Asn Gln Gln Lys Pro Gly Gln Pro Pro
        35                  40                  45

Arg Leu Leu Ile Tyr Leu Val Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ile Arg
                85                  90                  95

Glu Leu Thr Arg Ser Glu Gly Gly Pro Ser Trp Ser Gly Ala Tyr Thr
            100                 105                 110

Phe Gly Gly Gly Thr Lys Leu Glu Leu Lys Arg
        115                 120

<210> SEQ ID NO 26
<211> LENGTH: 124
<212> TYPE: PRT
<213> ORGANISM: Artificial Sequence
<220> FEATURE:
<223> OTHER INFORMATION: Synthetic construct

<400> SEQUENCE: 26

Asp Ile Val Met Thr Gln Ser Pro Ala Ser Leu Ala Val Ser Leu Gly
1               5                   10                  15

Gln Arg Ala Thr Ile Ser Tyr Arg Ala Ser Lys Ser Val Ser Thr Ser
            20                  25                  30

Gly Tyr Ser Tyr Met His Trp Asn Gln Gln Lys Pro Gly Gln Pro Pro
        35                  40                  45

Arg Leu Leu Ile Tyr Leu Val Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ile Arg
                85                  90                  95

Glu Leu Thr Arg Ser Glu Gly Gly Gln Ser Trp Lys Gly Ala Tyr Thr
            100                 105                 110

Phe Gly Gly Gly Thr Lys Leu Glu Ile Lys Arg Thr
        115                 120

<210> SEQ ID NO 27
<211> LENGTH: 124
<212> TYPE: PRT
<213> ORGANISM: Artificial Sequence
```

```
<220> FEATURE:
<223> OTHER INFORMATION: Synthetic construct

<400> SEQUENCE: 27

Asp Ile Val Met Thr Gln Ser Pro Ala Ser Leu Ala Val Ser Leu Gly
1               5                   10                  15

Gln Arg Ala Thr Ile Ser Tyr Arg Ala Ser Lys Ser Val Ser Thr Ser
            20                  25                  30

Gly Tyr Ser Tyr Met His Trp Asn Gln Gln Lys Pro Gly Gln Pro Pro
        35                  40                  45

Arg Leu Leu Ile Tyr Leu Val Ser Asn Leu Glu Ser Gly Val Pro Ala
    50                  55                  60

Arg Phe Ser Gly Ser Gly Ser Gly Thr Asp Phe Thr Leu Asn Ile His
65              70                  75                  80

Pro Val Glu Glu Glu Asp Ala Ala Thr Tyr Tyr Cys Gln His Ile Arg
                85                  90                  95

Glu Leu Thr Arg Ser Glu Gly Gly Pro Ser Trp Ser Gly Ala Tyr Thr
            100                 105                 110

Phe Gly Gly Gly Thr Lys Leu Glu Leu Lys Arg Thr
        115                 120

<210> SEQ ID NO 28
<211> LENGTH: 124
<212> TYPE: PRT
<213> ORGANISM: Artificial Sequence
<220> FEATURE:
<223> OTHER INFORMATION: Synthetic construct

<400> SEQUENCE: 28

Asp Ile Leu Met Thr Gln Ser Pro Ala Ser Leu Ala Val Ser Leu Gly
1               5                   10                  15

Gln Arg Ala Thr Ile Ser Tyr Arg Ala Ser Lys Ser Val Ser Thr Ser
            20                  25                  30

Gly Tyr Ser Tyr Met His Trp Asn Gln Gln Lys Pro Gly Gln Pro Pro
        35                  40                  45

Arg Leu Leu Ile Tyr Leu Val Ser Asn Leu Glu Ser Gly Val Pro Ala
    50                  55                  60

Arg Phe Ser Gly Ser Gly Ser Gly Thr Asp Phe Thr Leu Asn Ile His
65              70                  75                  80

Pro Val Glu Glu Glu Asp Ala Ala Thr Tyr Tyr Cys Gln His Ile Arg
                85                  90                  95

Glu Leu Thr Arg Ser Glu Gly Gly Pro Asn Trp Lys Gly Ala Tyr Thr
            100                 105                 110

Phe Gly Gly Gly Thr Lys Leu Glu Ile Lys Arg Thr
        115                 120

<210> SEQ ID NO 29
<211> LENGTH: 106
<212> TYPE: PRT
<213> ORGANISM: Artificial Sequence
<220> FEATURE:
<223> OTHER INFORMATION: Synthetic construct

<400> SEQUENCE: 29

Asp Ile Leu Met Thr Gln Ser Pro Ala Ser Leu Ala Val Ser Leu Gly
1               5                   10                  15

Gln Arg Ala Thr Ile Ser Tyr Arg Ala Ser Lys Ser Val Ser Thr Ser
            20                  25                  30
```

```
Gly Tyr Ser Tyr Met His Trp Asn Gln Gln Lys Pro Gly Gln Pro Pro
        35                  40              45

Arg Leu Leu Ile Tyr Leu Val Ser Asn Leu Glu Ser Gly Val Pro Ala
    50                  55              60

Arg Phe Ser Gly Ser Gly Ser Gly Thr Asp Phe Thr Leu Asn Ile His
65                  70                  75              80

Pro Val Glu Glu Glu Asp Ala Ala Thr Tyr Tyr Cys Gln His Ile Arg
                85                  90              95

Glu Leu Thr Arg Ser Glu Gly Gly Pro Ser
            100                 105
```

```
<210> SEQ ID NO 30
<211> LENGTH: 40
<212> TYPE: DNA
<213> ORGANISM: Artificial Sequence
<220> FEATURE:
<223> OTHER INFORMATION: Synthetic construct

<400> SEQUENCE: 30
gggcccaggc ggccgagctc gayatccagc tgactcagcc                             40
```

```
<210> SEQ ID NO 31
<211> LENGTH: 40
<212> TYPE: DNA
<213> ORGANISM: Artificial Sequence
<220> FEATURE:
<223> OTHER INFORMATION: Synthetic construct

<400> SEQUENCE: 31
gggcccaggc ggccgagctc gayattgttc tcwcccagtc                             40
```

```
<210> SEQ ID NO 32
<211> LENGTH: 40
<212> TYPE: DNA
<213> ORGANISM: Artificial Sequence
<220> FEATURE:
<223> OTHER INFORMATION: Synthetic construct

<400> SEQUENCE: 32
gggcccaggc ggccgagctc gayattgtgm tmactcagtc                             40
```

```
<210> SEQ ID NO 33
<211> LENGTH: 40
<212> TYPE: DNA
<213> ORGANISM: Artificial Sequence
<220> FEATURE:
<223> OTHER INFORMATION: Synthetic construct

<400> SEQUENCE: 33
gggcccaggc ggccgagctc gayattgtgy tracacagtc                             40
```

```
<210> SEQ ID NO 34
<211> LENGTH: 40
<212> TYPE: DNA
<213> ORGANISM: Artificial Sequence
<220> FEATURE:
<223> OTHER INFORMATION: Synthetic construct

<400> SEQUENCE: 34
gggcccaggc ggccgagctc gayattgtra tgacmcagtc                             40
```

```
<210> SEQ ID NO 35
<211> LENGTH: 40
<212> TYPE: DNA
```

-continued

```
<213> ORGANISM: Artificial Sequence
<220> FEATURE:
<223> OTHER INFORMATION: Synthetic construct

<400> SEQUENCE: 35
gggcccaggc ggccgagctc gayattmaga tramccagtc                          40

<210> SEQ ID NO 36
<211> LENGTH: 40
<212> TYPE: DNA
<213> ORGANISM: Artificial Sequence
<220> FEATURE:
<223> OTHER INFORMATION: Synthetic construct

<400> SEQUENCE: 36
gggcccaggc ggccgagctc gayattcaga tgaydcagtc                          40

<210> SEQ ID NO 37
<211> LENGTH: 40
<212> TYPE: DNA
<213> ORGANISM: Artificial Sequence
<220> FEATURE:
<223> OTHER INFORMATION: Synthetic construct

<400> SEQUENCE: 37
gggcccaggc ggccgagctc gayatycaga tgacacagac                          40

<210> SEQ ID NO 38
<211> LENGTH: 40
<212> TYPE: DNA
<213> ORGANISM: Artificial Sequence
<220> FEATURE:
<223> OTHER INFORMATION: Synthetic construct

<400> SEQUENCE: 38
gggcccaggc ggccgagctc gayattgttc tcawccagtc                          40

<210> SEQ ID NO 39
<211> LENGTH: 40
<212> TYPE: DNA
<213> ORGANISM: Artificial Sequence
<220> FEATURE:
<223> OTHER INFORMATION: Synthetic construct

<400> SEQUENCE: 39
gggcccaggc ggccgagctc gayattgwgc tsacccaatc                          40

<210> SEQ ID NO 40
<211> LENGTH: 40
<212> TYPE: DNA
<213> ORGANISM: Artificial Sequence
<220> FEATURE:
<223> OTHER INFORMATION: Synthetic construct

<400> SEQUENCE: 40
gggcccaggc ggccgagctc gayattstra tgacccartc                          40

<210> SEQ ID NO 41
<211> LENGTH: 40
<212> TYPE: DNA
<213> ORGANISM: Artificial Sequence
<220> FEATURE:
<223> OTHER INFORMATION: Synthetic construct

<400> SEQUENCE: 41
gggcccaggc ggccgagctc gayrttktga tgacccarac                          40
```

```
<210> SEQ ID NO 42
<211> LENGTH: 40
<212> TYPE: DNA
<213> ORGANISM: Artificial Sequence
<220> FEATURE:
<223> OTHER INFORMATION: Synthetic construct

<400> SEQUENCE: 42
gggcccaggc ggccgagctc gayattgtga tgacbcagkc                          40

<210> SEQ ID NO 43
<211> LENGTH: 40
<212> TYPE: DNA
<213> ORGANISM: Artificial Sequence
<220> FEATURE:
<223> OTHER INFORMATION: Synthetic construct

<400> SEQUENCE: 43
gggcccaggc ggccgagctc gayattgtga taacycagga                          40

<210> SEQ ID NO 44
<211> LENGTH: 40
<212> TYPE: DNA
<213> ORGANISM: Artificial Sequence
<220> FEATURE:
<223> OTHER INFORMATION: Synthetic construct

<400> SEQUENCE: 44
gggcccaggc ggccgagctc gayattgtga tgacccagwt                          40

<210> SEQ ID NO 45
<211> LENGTH: 40
<212> TYPE: DNA
<213> ORGANISM: Artificial Sequence
<220> FEATURE:
<223> OTHER INFORMATION: Synthetic construct

<400> SEQUENCE: 45
gggcccaggc ggccgagctc gayattgtga tgacacaacc                          40

<210> SEQ ID NO 46
<211> LENGTH: 40
<212> TYPE: DNA
<213> ORGANISM: Artificial Sequence
<220> FEATURE:
<223> OTHER INFORMATION: Synthetic construct

<400> SEQUENCE: 46
gggcccaggc ggccgagctc gayattttgc tgactcagtc                          40

<210> SEQ ID NO 47
<211> LENGTH: 42
<212> TYPE: DNA
<213> ORGANISM: Artificial Sequence
<220> FEATURE:
<223> OTHER INFORMATION: Synthetic construct

<400> SEQUENCE: 47
agatggtgca gccacagttc gtttkatttc cagyttggtc cc                       42

<210> SEQ ID NO 48
<211> LENGTH: 42
<212> TYPE: DNA
<213> ORGANISM: Artificial Sequence
<220> FEATURE:
```

<223> OTHER INFORMATION: Synthetic construct

<400> SEQUENCE: 48
agatggtgca gccacagttc gttttatttc caactttgtc cc                                    42

<210> SEQ ID NO 49
<211> LENGTH: 42
<212> TYPE: DNA
<213> ORGANISM: Artificial Sequence
<220> FEATURE:
<223> OTHER INFORMATION: Synthetic construct

<400> SEQUENCE: 49
agatggtgca gccacagttc gtttcagctc cagcttggtc cc                                    42

<210> SEQ ID NO 50
<211> LENGTH: 44
<212> TYPE: DNA
<213> ORGANISM: Artificial Sequence
<220> FEATURE:
<223> OTHER INFORMATION: Synthetic construct

<400> SEQUENCE: 50
gctgcccaac cagccatggc cctcgaggtr magcttcagg agtc                                  44

<210> SEQ ID NO 51
<211> LENGTH: 44
<212> TYPE: DNA
<213> ORGANISM: Artificial Sequence
<220> FEATURE:
<223> OTHER INFORMATION: Synthetic construct

<400> SEQUENCE: 51
gctgcccaac cagccatggc cctcgaggtb cagctbcagc agtc                                  44

<210> SEQ ID NO 52
<211> LENGTH: 44
<212> TYPE: DNA
<213> ORGANISM: Artificial Sequence
<220> FEATURE:
<223> OTHER INFORMATION: Synthetic construct

<400> SEQUENCE: 52
gctgcccaac cagccatggc cctcgaggtg cagctgaags astc                                  44

<210> SEQ ID NO 53
<211> LENGTH: 44
<212> TYPE: DNA
<213> ORGANISM: Artificial Sequence
<220> FEATURE:
<223> OTHER INFORMATION: Synthetic construct

<400> SEQUENCE: 53
gctgcccaac cagccatggc cctcgaggtc carctgcaac artc                                  44

<210> SEQ ID NO 54
<211> LENGTH: 43
<212> TYPE: DNA
<213> ORGANISM: Artificial Sequence
<220> FEATURE:
<223> OTHER INFORMATION: Synthetic construct

<400> SEQUENCE: 54
gctgcccaac cagccatggc cctcgaggtb cagctbcagc art                                   43

-continued

```
<210> SEQ ID NO 55
<211> LENGTH: 44
<212> TYPE: DNA
<213> ORGANISM: Artificial Sequence
<220> FEATURE:
<223> OTHER INFORMATION: Synthetic construct

<400> SEQUENCE: 55
gctgcccaac cagccatggc cctcgaggty carctgcagc agtc                       44

<210> SEQ ID NO 56
<211> LENGTH: 44
<212> TYPE: DNA
<213> ORGANISM: Artificial Sequence
<220> FEATURE:
<223> OTHER INFORMATION: Synthetic construct

<400> SEQUENCE: 56
gctgcccaac cagccatggc cctcgaggtc cacgtgaagc agtc                       44

<210> SEQ ID NO 57
<211> LENGTH: 44
<212> TYPE: DNA
<213> ORGANISM: Artificial Sequence
<220> FEATURE:
<223> OTHER INFORMATION: Synthetic construct

<400> SEQUENCE: 57
gctgcccaac cagccatggc cctcgaggtg aasstggtgg aatc                       44

<210> SEQ ID NO 58
<211> LENGTH: 44
<212> TYPE: DNA
<213> ORGANISM: Artificial Sequence
<220> FEATURE:
<223> OTHER INFORMATION: Synthetic construct

<400> SEQUENCE: 58
gctgcccaac cagccatggc cctcgaggtg awgytggtgg agtc                       44

<210> SEQ ID NO 59
<211> LENGTH: 43
<212> TYPE: DNA
<213> ORGANISM: Artificial Sequence
<220> FEATURE:
<223> OTHER INFORMATION: Synthetic construct

<400> SEQUENCE: 59
gctgcccaac cagccatggc cctcgaggtg cagskggtgg agt                        43

<210> SEQ ID NO 60
<211> LENGTH: 44
<212> TYPE: DNA
<213> ORGANISM: Artificial Sequence
<220> FEATURE:
<223> OTHER INFORMATION: Synthetic construct

<400> SEQUENCE: 60
gctgcccaac cagccatggc cctcgaggtg camctggtgg agtc                       44

<210> SEQ ID NO 61
<211> LENGTH: 44
<212> TYPE: DNA
<213> ORGANISM: Artificial Sequence
<220> FEATURE:
<223> OTHER INFORMATION: Synthetic construct
```

-continued

<400> SEQUENCE: 61
gctgcccaac cagccatggc cctcgaggtg aagctgatgg artc                    44

<210> SEQ ID NO 62
<211> LENGTH: 44
<212> TYPE: DNA
<213> ORGANISM: Artificial Sequence
<220> FEATURE:
<223> OTHER INFORMATION: Synthetic construct

<400> SEQUENCE: 62
gctgcccaac cagccatggc cctcgaggtg carcttgttg agtc                    44

<210> SEQ ID NO 63
<211> LENGTH: 44
<212> TYPE: DNA
<213> ORGANISM: Artificial Sequence
<220> FEATURE:
<223> OTHER INFORMATION: Synthetic construct

<400> SEQUENCE: 63
gctgcccaac cagccatggc cctcgaggtr aagcttctcg agtc                    44

<210> SEQ ID NO 64
<211> LENGTH: 44
<212> TYPE: DNA
<213> ORGANISM: Artificial Sequence
<220> FEATURE:
<223> OTHER INFORMATION: Synthetic construct

<400> SEQUENCE: 64
gctgcccaac cagccatggc cctcgaggtg aarsttgagg agtc                    44

<210> SEQ ID NO 65
<211> LENGTH: 46
<212> TYPE: DNA
<213> ORGANISM: Artificial Sequence
<220> FEATURE:
<223> OTHER INFORMATION: Synthetic construct

<400> SEQUENCE: 65
gctgcccaac cagccatggc cctcgaggtt actctraaag wgtstg                  46

<210> SEQ ID NO 66
<211> LENGTH: 44
<212> TYPE: DNA
<213> ORGANISM: Artificial Sequence
<220> FEATURE:
<223> OTHER INFORMATION: Synthetic construct

<400> SEQUENCE: 66
gctgcccaac cagccatggc cctcgaggtc caactvcagc arcc                    44

<210> SEQ ID NO 67
<211> LENGTH: 44
<212> TYPE: DNA
<213> ORGANISM: Artificial Sequence
<220> FEATURE:
<223> OTHER INFORMATION: Synthetic construct

<400> SEQUENCE: 67
gctgcccaac cagccatggc cctcgaggtg aacttggaag tgtc                    44

<210> SEQ ID NO 68
<211> LENGTH: 44

```
<212> TYPE: DNA
<213> ORGANISM: Artificial Sequence
<220> FEATURE:
<223> OTHER INFORMATION: Synthetic construct

<400> SEQUENCE: 68
gctgcccaac cagccatggc cctcgaggtg aaggtcatcg agtc                        44

<210> SEQ ID NO 69
<211> LENGTH: 42
<212> TYPE: DNA
<213> ORGANISM: Artificial Sequence
<220> FEATURE:
<223> OTHER INFORMATION: Synthetic construct

<400> SEQUENCE: 69
cgatgggccc ttggtggagg ctgaggagac ggtgaccgtg gt                          42

<210> SEQ ID NO 70
<211> LENGTH: 42
<212> TYPE: DNA
<213> ORGANISM: Artificial Sequence
<220> FEATURE:
<223> OTHER INFORMATION: Synthetic construct

<400> SEQUENCE: 70
cgatgggccc ttggtggagg ctgaggagac tgtgagagtg gt                          42

<210> SEQ ID NO 71
<211> LENGTH: 42
<212> TYPE: DNA
<213> ORGANISM: Artificial Sequence
<220> FEATURE:
<223> OTHER INFORMATION: Synthetic construct

<400> SEQUENCE: 71
cgatgggccc ttggtggagg ctgcagagac agtgaccaga gt                          42

<210> SEQ ID NO 72
<211> LENGTH: 42
<212> TYPE: DNA
<213> ORGANISM: Artificial Sequence
<220> FEATURE:
<223> OTHER INFORMATION: Synthetic construct

<400> SEQUENCE: 72
cgatgggccc ttggtggagg ctgaggagac ggtgactgag gt                          42

<210> SEQ ID NO 73
<211> LENGTH: 317
<212> TYPE: PRT
<213> ORGANISM: Artificial Sequence
<220> FEATURE:
<223> OTHER INFORMATION: Synthetic construct

<400> SEQUENCE: 73

Met Phe Gln Ala Ala Glu Arg Pro Gln Glu Trp Ala Met Glu Gly Pro
1               5                   10                  15

Arg Asp Gly Leu Lys Lys Glu Arg Leu Leu Asp Asp Arg His Asp Ser
            20                  25                  30

Gly Leu Asp Ser Met Lys Asp Glu Glu Tyr Glu Gln Met Val Lys Glu
        35                  40                  45

Leu Gln Glu Ile Arg Leu Glu Pro Gln Glu Val Pro Arg Gly Ser Glu
    50                  55                  60
```

-continued

```
Pro Trp Lys Gln Gln Leu Thr Glu Asp Gly Asp Ser Phe Leu His Leu
65                  70                  75                  80

Ala Ile Ile His Glu Glu Lys Ala Leu Thr Met Glu Val Ile Arg Gln
                85                  90                  95

Val Lys Gly Asp Leu Ala Phe Leu Asn Phe Gln Asn Asn Leu Gln Gln
                100                 105                 110

Thr Pro Leu His Leu Ala Val Ile Thr Asn Gln Pro Glu Ile Ala Glu
                115                 120                 125

Ala Leu Leu Gly Ala Gly Cys Asp Pro Glu Leu Arg Asp Phe Arg Gly
                130                 135                 140

Asn Thr Pro Leu His Leu Ala Cys Glu Gln Gly Cys Leu Ala Ser Val
145                 150                 155                 160

Gly Val Leu Thr Gln Ser Cys Thr Thr Pro His Leu His Ser Ile Leu
                165                 170                 175

Lys Ala Thr Asn Tyr Asn Gly His Thr Cys Leu His Leu Ala Ser Ile
                180                 185                 190

His Gly Tyr Leu Gly Ile Val Glu Leu Leu Val Ser Leu Gly Ala Asp
                195                 200                 205

Val Asn Ala Gln Glu Pro Cys Asn Gly Arg Thr Ala Leu His Leu Ala
                210                 215                 220

Val Asp Leu Gln Asn Pro Asp Leu Val Ser Leu Leu Leu Lys Cys Gly
225                 230                 235                 240

Ala Asp Val Asn Arg Val Thr Tyr Gln Gly Tyr Ser Pro Tyr Gln Leu
                245                 250                 255

Thr Trp Gly Arg Pro Ser Thr Arg Ile Gln Gln Gln Leu Gly Gln Leu
                260                 265                 270

Thr Leu Glu Asn Leu Gln Met Leu Pro Glu Ser Glu Asp Glu Glu Ser
                275                 280                 285

Tyr Asp Thr Glu Ser Glu Phe Thr Glu Phe Thr Glu Asp Glu Leu Pro
                290                 295                 300

Tyr Asp Asp Cys Val Phe Gly Gly Gln Arg Leu Thr Leu
305                 310                 315
```

```
<210> SEQ ID NO 74
<211> LENGTH: 317
<212> TYPE: PRT
<213> ORGANISM: Artificial Sequence
<220> FEATURE:
<223> OTHER INFORMATION: Synthetic construct

<400> SEQUENCE: 74
```

```
Met Phe Gln Ala Ala Glu Arg Pro Gln Glu Trp Ala Met Glu Gly Pro
1                   5                   10                  15

Arg Asp Gly Leu Lys Lys Glu Arg Leu Leu Asp Asp Arg His Asp Ala
                20                  25                  30

Gly Leu Asp Ala Met Lys Asp Glu Glu Tyr Glu Gln Met Val Lys Glu
                35                  40                  45

Leu Gln Glu Ile Arg Leu Glu Pro Gln Glu Val Pro Arg Gly Ser Glu
                50                  55                  60

Pro Trp Lys Gln Gln Leu Thr Glu Asp Gly Asp Ser Phe Leu His Leu
65                  70                  75                  80

Ala Ile Ile His Glu Glu Lys Ala Leu Thr Met Glu Val Ile Arg Gln
                85                  90                  95

Val Lys Gly Asp Leu Ala Phe Leu Asn Phe Gln Asn Asn Leu Gln Gln
                100                 105                 110
```

-continued

```
Thr Pro Leu His Leu Ala Val Ile Thr Asn Gln Pro Glu Ile Ala Glu
    115                 120                 125

Ala Leu Leu Gly Ala Gly Cys Asp Pro Glu Leu Arg Asp Phe Arg Gly
    130                 135                 140

Asn Thr Pro Leu His Leu Ala Cys Glu Gln Gly Cys Leu Ala Ser Val
145                 150                 155                 160

Gly Val Leu Thr Gln Ser Cys Thr Thr Pro His Leu His Ser Ile Leu
                165                 170                 175

Lys Ala Thr Asn Tyr Asn Gly His Thr Cys Leu His Leu Ala Ser Ile
                180                 185                 190

His Gly Tyr Leu Gly Ile Val Glu Leu Leu Val Ser Leu Gly Ala Asp
                195                 200                 205

Val Asn Ala Gln Glu Pro Cys Asn Gly Arg Thr Ala Leu His Leu Ala
    210                 215                 220

Val Asp Leu Gln Asn Pro Asp Leu Val Ser Leu Leu Leu Lys Cys Gly
225                 230                 235                 240

Ala Asp Val Asn Arg Val Thr Tyr Gln Gly Tyr Ser Pro Tyr Gln Leu
                245                 250                 255

Thr Trp Gly Arg Pro Ser Thr Arg Ile Gln Gln Gln Leu Gly Gln Leu
                260                 265                 270

Thr Leu Glu Asn Leu Gln Met Leu Pro Glu Ser Glu Asp Glu Glu Ser
                275                 280                 285

Tyr Asp Thr Glu Ser Glu Phe Thr Glu Phe Thr Glu Asp Glu Leu Pro
    290                 295                 300

Tyr Asp Asp Cys Val Phe Gly Gly Gln Arg Leu Thr Leu
305                 310                 315

<210> SEQ ID NO 75
<211> LENGTH: 13
<212> TYPE: PRT
<213> ORGANISM: Artificial Sequence
<220> FEATURE:
<223> OTHER INFORMATION: Synthetic construct

<400> SEQUENCE: 75

Asp Arg Gly Asp Ala Gly Leu Asp Ala Met Lys Asp Glu
1               5                   10

<210> SEQ ID NO 76
<211> LENGTH: 13
<212> TYPE: PRT
<213> ORGANISM: Artificial Sequence
<220> FEATURE:
<223> OTHER INFORMATION: Synthetic construct

<400> SEQUENCE: 76

Asp Arg Gly Asp Ser Gly Leu Asp Ser Met Lys Asp Glu
1               5                   10
```

ANTIBODY BINDING TO SUPER-REPRESSOR IκB (SRIκB) OR ANTIGEN BINDING FRAGMENT THEREOF

SEQUENCE LISTING SUBMISSION VIA EFS-WEB

A computer readable text file, entitled "SequenceListing.txt," created on Aug. 6, 2025 with a file size of 40,354 bytes contains the sequence listing for this application and is hereby incorporated by reference in its entirety.

BACKGROUND OF THE INVENTION

1. Field of the Invention

The present disclosure relates to a monoclonal or polyclonal antibody specifically recognizing Super-repressor IκB (srIκB) or an antigen-binding fragment thereof, a nucleic acid encoding the same, a vector including the nucleic acid, a host cell into which the nucleic acid or the vector is introduced, use of the antibody or the antigen-binding fragment thereof, and a preparation method thereof.

2. Description of the Related Art

Although inflammatory responses are the body's defense mechanism against various stimuli, chronic inflammatory responses may lead to various diseases including arthritis, hepatitis, septic shock, neuropathic disorders, etc. (Chung et al., *Clin. Rheumatol.* 26:12281233, 2007).

Macrophages have an important role in several inflammatory responses (Mayeux et al., *J. Toxicol. Environ. Health.* 51:415435, 1997), and LPS activates macrophages that produce inflammatory mediators such as nitric oxide (NO), prostaglandin E2 (PGE2), etc., and inflammatory cytokines such as tumor necrosis factor-α (TNF-α), interleukin-1 (IL-1), etc. (Takeuchi et al., *J. Biol. Chem.* 281: 2136221368, 2006). Inducible nitric oxide synthase (iNOS) promotes the formation of excess nitric oxide that may lead to inflammatory diseases (Nathan et al., *Curr. Opin. Immunol.* 3:6570, 1991), and cyclooxygenase-2 (COX-2) is induced by inflammatory stimuli and responses for the synthesis of PGE2 (Yoon et al., *J. Biosci. Bioeng.* 107: 429438, 2009). Thus, overexpression of NO and PGE2 by iNOS and COX-2 has an important role in the regulation of inflammatory responses.

NF-κB is a transcrptional regulator that induces the expression of genes involved in different processes of immune and inflammatory responses, and structurally consists of NF-κB1(p50), NF-κB2(p52), RelA(p65), RelB, and c-Rel, and is known to mediate transcription of target genes by binding as various hetero- or homo-dimers to specific DNA elements. Binding of NF-κB with IκB in the cytoplasm inhibits its translocation into the nucleus, and thus transcription is inhibited. This is because the C-terminal portions of p100 and p105, which are the precursor proteins of NF-κB, are very similar to those of IκB, and thus the function of NF-κB is inhibited.

NF-κB is a major transcription factor that induces inflammatory responses, and mainly regulates the expression of genes related to inflammation in immune cells and various other cells. Therefore, since excessive activation of the NF-κB signaling pathway causes various inflammatory diseases, selective inhibition of the excessively activated NF-κB pathway in inflammatory cells may be an effective therapeutic strategy for intractable chronic inflammatory diseases such as rheumatoid arthritis, sepsis, psoriasis, etc. In addition, since activation of NF-κB increases expression of factors capable of inhibiting apoptosis and thus serves to inhibit apoptosis, continuous activation of the NF-κB signaling pathway in cancer cells acts as a major cause of resistance to anticancer treatment, causing a reduction in the therapeutic effects of anticancer agents.

In unstimulated normal cells, most NF-κB exists in an inactive form in the cytoplasm through binding with its inhibitory protein, IκB. IκB Kinase (IKK) complex activated by various stimuli such as TNF-α, LPS, etc. phosphorylates IκB, and the phosphorylated IκB is ubiquitinated and consequently degraded through the proteasome. When IκB is degraded, NF-κB (p50/p65) bound thereto is released in a free state in the cytoplasm, passes through the nuclear membrane, and then binds to a promoter region of a target gene in the nucleus to promote the mRNA transcription process, and is an important component of inflammatory responses that induce transcription of inflammatory mediators and inflammatory cytokines such as iNOS, COX-2, NO, PGE2, TNF-α, IL-1, etc. (Lappas et al., *Biol. Reprod.* 67:668673, 2002).

Super-repressor IκB (srIκB), which is S32A and S36A mutant form of IκB, is not phosphorylated by IKK and is not degraded by proteasome, and as a result, it has a function capable of continuously inhibiting NF-κB. Therefore, srIκB has great potential as a therapeutic agent for various inflammatory disease models.

On the other hand, an antibody is a biomolecule that is most frequently used in relation to protein utilization such as protein sensing, detection, purification, fixation, activity regulation, targeting, etc. In order to use proteins in various fields such as medical and pharmaceutical fields, it is necessary to develop antibodies specific to target proteins.

With regard to the use of srIκB, the present inventors prepared exosomes loading super-repressor IκB protein, as in Korean Patent No. 10-1877010, and they found that super-repressor IκB protein is released into the cytoplasm of target cells when treated with the exosomes, and it is possible to use the exosome loading the super-repressor IκB of the invention as a therapeutic agent for inflammatory diseases, particularly sepsis and arthritis. "A method of preparing exosomes loading super-repressor-IκB protein and a pharmaceutical composition for preventing and treating inflammatory diseases, the pharmaceutical composition including, as an active ingredient, the exosomes prepared by the preparation method" has been registered.

An antibody specifically binding to srIκB by distinguishing it from a wild-type IκB is required as an antibody for use in srIκB cargo protein for loading srIκB into exosomes and in various analysis and efficacy experiments (W/B, FACS, IIP, ELISA, etc.). However, srIκB, which is an S32A and S36A mutant form of IκB, has an extremely similar sequence in which only two amino acids are changed, and the mutated sequences are close to each other. For this reason, the srIκB-specific antibody has difficulties in distinguishing the mutated amino acid sites and specifically binding only to the corresponding amino acid sites. Until now, there has been no report of an anti-srIκB antibody that specifically binds to srIκB by distinguishing it from the wild-type IκB.

In view of this technical background, the present inventors have endeavored to develop an antibody that specifically binds to srIκB. As a result, the present inventors have developed an anti-srIκB antibody that specifically binds to srIκB. and they found that the antibody binds to srIκB with a remarkably higher affinity than IκB, thereby completing the present invention.

SUMMARY OF THE INVENTION

An object of the present disclosure is to provide a novel anti-srIκB antibody specifically binding to srIκB or an antigen-binding fragment thereof.

Another object of the present disclosure is to provide a nucleic acid encoding the antibody or the antigen-binding fragment thereof.

Still another object of the present disclosure is to provide use of the anti-srIκB antibody.

Still another object of the present disclosure is to provide a vector including the nucleic acid, a host cell into which the nucleic acid or the vector is introduced, and a method of preparing the SrIκB antibody.

To achieve the above object, the present disclosure provides an antibody specifically binding to srIκB, the antibody including a heavy chain variable region including a heavy chain CDR1 represented by SEQ ID NO: 3; a heavy chain CDR2 represented by SEQ ID NO: 4; and a heavy chain CDR3 represented by SEQ ID NO: 5, or an antigen-binding fragment thereof.

Further, the present disclosure provides an antibody specifically binding to SrIκB, the antibody including a light chain variable region including a light chain CDR1 represented by SEQ ID NO: 6; a light chain CDR2 represented by SEQ ID NO: 7; and a light chain CDR3 represented by SEQ ID NO: 8, or an antigen-binding fragment thereof.

Further, the present disclosure provides a nucleic acid encoding the antibody or the antigen-binding fragment thereof.

Further, the present disclosure provides a vector including the nucleic acid.

Further, the present disclosure provides a host cell into which the nucleic acid or the vector is introduced.

Further, the present disclosure provides a composition for sensing, detecting, purifying, or targeting srIκB protein, and/or identifying activity thereof, the composition including the antibody or the antigen-binding fragment thereof.

Further, the present disclosure provides use of the antibody or the antigen-binding fragment thereof in sensing, detecting, purifying, or targeting srIκB protein, and/or identifying activity thereof.

Further, the present disclosure provides a method of preparing the antibody or the antigen-binding fragment thereof, the method including the steps of culturing the cells of the present disclosure; and collecting the antibody or the antigen-binding fragment thereof from the cultured cells.

BRIEF DESCRIPTION OF THE DRAWINGS

FIG. 4 shows results of examining activities of polyclonal antibodies, in which the polyclonal antibodies were isolated by ELISA after 1:100-1:100,000 dilution of the sera obtained through $3^{rd}$ bleeding after boosting;

FIG. 5 shows results of examining specificities of polyclonal antibodies isolated and purified, in which the specificities of the antibodies were examined using serum #1 and serum #2 of anti-srIκB polyclonal antibody and using srIκB-introduced cells in Western blotting using the antibody obtained in the $3^{rd}$ bleeding:

FIG. 6 shows a schematic illustration of Abclon-MANI protocol by Abclon, which is a process of preparing the antibody of an exemplary embodiment of the present disclosure;

FIG. 7 shows a schematic illustration of workflow for the preparation of a hybridoma cell line of the anti-srIκB antibody, in which mouse adaptation, pristane injection, hybridoma cell injection, ascites isolation, and SDS-PAGE were performed at week 0, week 1, week 2, week 4, and week 5, respectively;

FIG. 8 shows the results of the $1^{st}$ through a fusion screening method (ELISA), in which clones with an O.D. value of 0.5 or more were selected, and based on the selected clones, binding to srIκB peptide, WT IκB peptide, Lysate, and SMCC control was reexamined to select six kinds of clones;

FIG. 9 shows the results of examining the band of the target protein through Western blotting of the selected six kinds of clones;

FIG. 10 shows the results of immunoprecipitation (IP) performed using cell culture supernatant to reexamine binding specificity of the srIκB peptide-specific antibody clones selected through ELISA;

FIG. 11 shows the results of ELISA to examine binding specificity of the selected four antibodies using a cell line producing srIκB-loaded exosomes;

FIG. 12 shows the results of isotype screening for the selected clones using culture supernatant of the cell line producing srIκB-loaded exosomes;

FIG. 13 shows the results of ELISA of ultimately selected two clones 2F8 and 5A2 by ascites purification, in which the final 2F8 and 5A2 antibodies showed an O.D. value of 1.0 or more in the dilution even at a high dilution rate;

FIG. 14 shows the results of performing an antibody affinity test using antibodies isolated from the selected four hybridoma cell lines and the culture supernatant of the cell line producing srIκB-loaded exosomes; and FIG. 15 shows the results of examining srIκB-binding specificity of 2F8 and 5A2 antibodies, which are the two clones ultimately selected, according to dilution rates.

DETAILED DESCRIPTION OF THE
PREFERRED EMBODIMENTS

Unless defined otherwise, all technical and scientific terms used herein have the same meanings as those generally understood by one of ordinary skill in the art to which the present disclosure belongs.

Generally, the nomenclature used herein is well known and commonly employed in the art.

Currently, no commercially available antibodies that specifically bind to srIκB protein have been developed, and antibodies used in research using srIκB protein are antibodies binding to IκB, and cannot specifically distinguish between srIκB and IκB proteins. srIκB, which is an S32A and S36A mutant form of IκB, has an extremely similar sequence in which only two amino acids are changed, and the mutated sequences are close to each other. For this reason, the srIκB-specific antibody has difficulties in distinguishing the mutated amino acid sites and specifically binding only to the corresponding amino acid sites.

In one embodiment of the present disclosure, a novel anti-srIκB antibody binding to srIκB with high affinity was screened, and the anti-srIκB antibody ultimately screened was found to specifically bind to srIκB by distinguishing it from the wild-type IκB.

Accordingly, one aspect of the present disclosure relates to an antibody binding to srIκB, the antibody including a heavy chain variable region including a heavy chain CDR1 represented by SEQ ID NO: 3, a heavy chain CDR2 represented by SEQ ID NO: 4, and a heavy chain CDR3 represented by SEQ ID NO: 5, or an antigen-binding fragment thereof.

Another aspect of the present disclosure relates to an antibody binding to SrIκB, the antibody including a light chain variable region including a light chain CDR1 represented by SEQ ID NO: 6, a light chain CDR2 represented by SEQ ID NO: 7, and a light chain CDR3 represented by SEQ ID NO: 8, or an antigen-binding fragment thereof.

Preferably, the present disclosure may be characterized by including the heavy chain variable region including the heavy chain CDR1 represented by SEQ ID NO: 3, the heavy chain CDR2 represented by SEQ ID NO: 4, and the heavy chain CDR3 represented by SEQ ID NO: 5; and the light chain variable region including the light chain CDR1 represented by SEQ ID NO: 6, the light chain CDR2 represented by SEQ ID NO: 7, and the light chain CDR3 represented by SEQ ID NO: 8.

Figure 1:
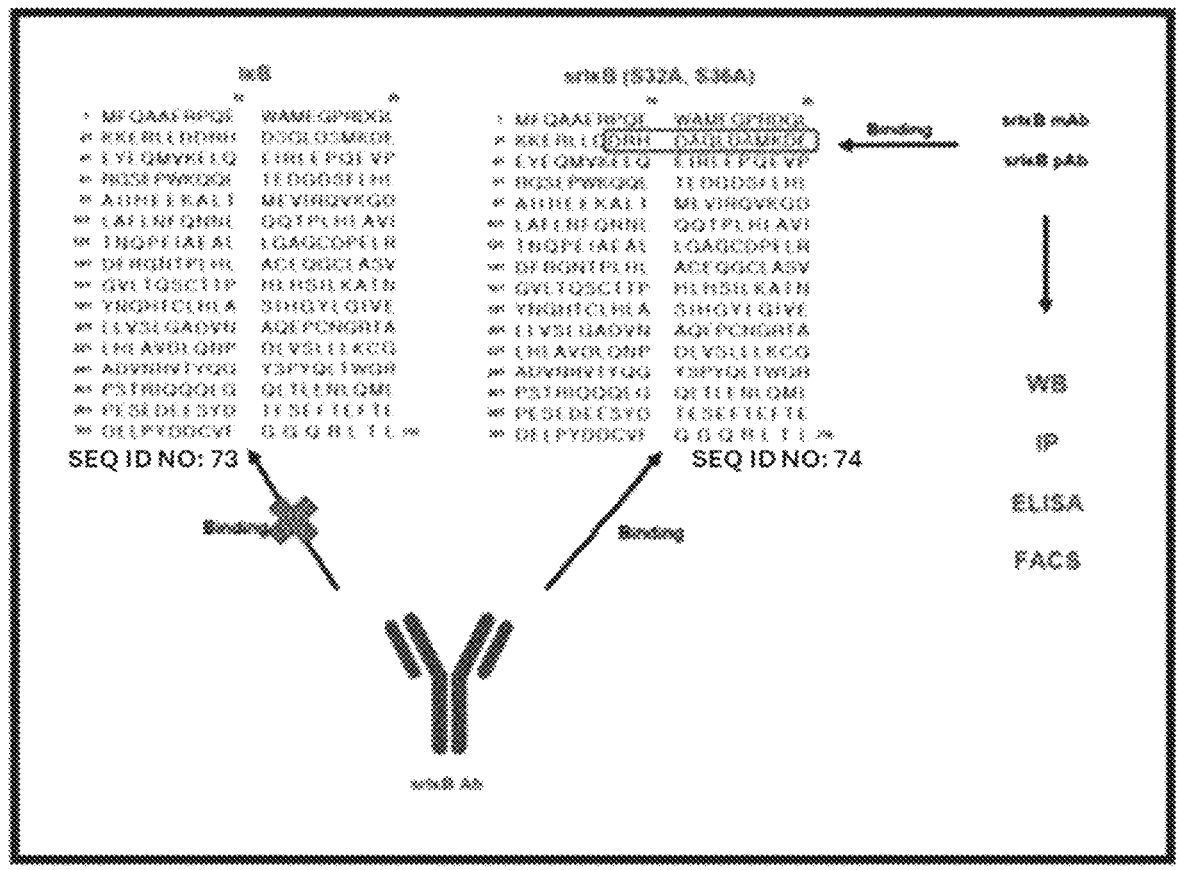
FIG. 1 shows comparison of a sequence of the wild-type IκB (WT IκB) and an amino acid sequence of Super-repressor IκB (srIκB), in which the red box indicates a peptide sequence used for screening in an exemplary embodiment of the present disclosure.

As used herein, the "super-repressor IκB (srIκB: SEQ ID NO: 74)" is a S32A, S36A mutant form which is a protein involved in the NF-κB pathway (FIG. 1).

Super-repressor IκB (srIκB) is not phosphorylated by IKK and is not degraded by proteasome, and as a result, it has a function capable of continuously inhibiting the NF-κB-related intracellular signaling pathway by blocking nuclear translocation of NF-κB.

With regard to the use of srIκB, the present inventors prepared exosomes loading Super-repressor IκB protein, as in Korean Patent No. 10-1877010, and they found that Super-repressor IκB protein is delivered into the cytoplasm of target cells when treated with the exosomes, and the exosome loading the super-repressor IκB of the invention may be used as a therapeutic agent for inflammatory diseases. "A method of preparing exosomes loading super-repressor-IκB protein and a pharmaceutical composition for preventing and treating inflammatory diseases, the pharmaceutical composition including, as an active ingredient, the exosomes prepared by the preparation method" has been registered.

As used herein, the term "antibody" refers to a collection of antibody protein molecules including one or more complementarity determining regions, one antibody protein molecule, or derivatives thereof.

As used herein, the term "antibody binding to srIκB" is a concept including both polyclonal antibody and monoclonal antibody, preferably, a monoclonal antibody, and it may have an intact whole antibody form, but is not limited thereto. The scope of the present disclosure includes an intact antibody form specifically binding to srIκB as well as an antigen-binding fragment of the antibody molecule. As used herein the "antibody binding to srIκB" may be used interchangeably with "srIκB antibody" or "anti-srIκB antibody".

The antibody binding to srIκB of the present disclosure or the antigen-binding fragment thereof may be characterized by specifically binding to srIκB by distinguishing it from the wild-type IκB. As used herein, "specifically binding to srIκB by distinguishing it from the wild-type IκB" means exhibiting a significantly higher binding affinity to srIκB than the wild-type IκB. For example, the antibody may exhibit about 1.1 times, about 1.2 times, about 1.3 times, about 1.4 times, about 1.5 times, about 1.6 times, about 1.7 times, about 1.8 times, about 1.9 times, or about 2.0 times or more, preferably, about 1.5 times or more binding affinity to srIκB than the wild-type IκB, but is not limited thereto.

In general, an intact antibody has a structure having two full-length light chains and two full-length heavy chains, each light chain linked with the heavy chain via a disulfide bond. The heavy chain constant region has gamma (γ), mu (μ), alpha (α), delta (δ), and epsilon (ε) types, and the subclasses include gamma1 (γ1), gamma2 (γ2), gamma3 (γ3), gamma4 (γ4), alpha1 (α1), and alpha2 (α2). The light chain constant region has kappa (κ) and lambda (λ) types.

As used herein, the "antigen-binding fragment" refers to a fragment retaining a function of recognizing and binding to the antigen of the anti-srIκB antibody, i.e., srIκB, and is a concept including Fab, Fab', F(ab')₂, scFv, dsFv, Fv, etc., and in the present disclosure, it may be used interchangeably with "antibody fragment".

In the present disclosure, the antibody may be characterized by specifically binding to srIκB while not binding to the wild-type IκB. Preferably, the antibody may be characterized by specifically binding to a site including mutation sites (S32A and S36A) of srIκB, but is not limited thereto. An intact antibody specifically binding to srIκB, as well as a variant, derivative, or antigen-binding fragment thereof may be included in the scope of the present disclosure.

As used herein, the term "monoclonal antibody" refers to an antibody obtained from a population of substantially homogeneous antibodies, i.e., individual antibodies occupying the population that are identical except for possible naturally occurring mutations that may be present in minor amounts. Monoclonal antibodies are highly specific, being directed against a single antigenic site. In contrast to polyclonal antibody preparations which generally include different antibodies directed against different determinants (epitopes), each monoclonal antibody is directed against a single determinant on the antigen.

As used herein, the term "polyclonal antibody" refers to a composition of different antibody molecules capable of binding to or reacting with one or more immunogenic determinants or epitopes on the same or different antigens. The individual antibodies in the composition may be characterized by being different from each other, and each may bind to or react with a specific epitope. For example, diversity of polyclonal antibody may be generally determined by a variable region of the antibody, for example, the complementarity determining regions (CDR1, CDR2, and CDR3) of light or heavy chain. In addition, the polyclonal antibody may be attributed to differences between individual antibody molecules present in the constant region, and for example, it may be an antibody mixture including two or more different antibody isotypes, such as human isotype IgG1, IgG2, IgG3, IgG4, IgA1, IgA2, IgM, IgD, and IgE, or murine isotype IgG1, IgG2a, IgG2b, IgG3, and IgA.

In the present disclosure, the polyclonal antibody may be isolated or identified and purified from mammalian blood, secretions, other body fluids, reproductive cells, etc., may include a mixture of different monoclonal antibodies, and may be prepared as a recombinant polyclonal antibody.

The "recombinant polyclonal antibody" refers to a polyclonal antibody prepared by recombinant technology, and each antibody molecule in the polyclonal antibody exhibits a desired binding activity to a target antigen consisting of one or more epitopes.

The "antigen-binding fragment" of an antibody or the "antibody fragment" refers to a fragment that retains an antigen-binding function, and includes Fab, F(ab'), F(ab')$_2$, Fv, etc. Among the antibody fragments, Fab has a structure of having light chain and heavy chain variable regions, a light chain constant region, and a first heavy chain constant region (CH1), and has one antigen binding site. Fab' is different from Fab in that Fab' has a hinge region including one or more cysteine residues at the C-terminus of the heavy chain CH1 domain. F(ab')$_2$ antibody is generated through a disulfide bond formed between the cysteine residues in the hinge regions of Fab'. Fv is a minimal antibody segment having only a heavy chain variable region and a light chain variable region. A two-chain Fv has a structure in which a heavy chain variable region and a light chain variable region are linked through a noncovalent linkage, and a single-chain Fv (scFv) includes a heavy chain variable region and a light chain variable region covalently linked to each other via a peptide linker or directly linked at the C-terminus, thereby forming a dimeric structure as in the double-chain Fv. These antibody fragments may be obtained using proteases (e.g., the whole antibody is digested with papain to obtain Fab fragments, and is digested with pepsin to obtain F(ab')$_2$ fragments), and may be prepared by a genetic recombinant technique.

In one embodiment, the antibody according to the present disclosure is in the form of Fv (e.g., scFv) or the whole antibody. In addition, the heavy chain constant region may be selected from any one isotype of gamma ($\gamma$), mu (m), alpha ($\alpha$), delta ($\delta$), and epsilon ($\delta$) types. For example, the constant region may be gamma1 (IgG1), gamma3 (IgG3), or gamma4 (IgG4). The light chain constant region may be a kappa or lambda type.

In the present disclosure, the heavy chain constant region of the antibody or antigen-binding fragment may be an IgG1 isotype.

In the present disclosure, the light chain constant region of the antibody or antigen-binding fragment may be a kappa isotype.

In the present disclosure, it is most preferable that the heavy chain constant region of the antibody or antigen-binding fragment may be an IgG1 isotype, and the light chain constant region thereof may be a kappa isotype, but is not limited thereto.

As used herein, the term "heavy chain" refers to the full-length heavy chain and fragments thereof, the full-length heavy chain including a variable region domain VH that includes an amino acid sequence having a variable region sequence sufficient to impart specificity to an antigen, and three constant region domains, CH1, CH2, and CH3. In addition, as used herein, the term "light chain" refers to the full-length light chain and fragments thereof, the full-length light chain including a variable region domain VL that includes an amino acid sequence having a variable region sequence sufficient to impart specificity to an antigen, and a constant domain CL.

The antibody of the present disclosure may include monoclonal antibodies, multi-specific antibodies, human antibodies, humanized antibodies, chimeric antibodies, single chain Fvs (scFVs), single chain antibodies, Fab fragments, F(ab') fragments, disulfide-linked Fvs (sdFVs), and anti-idiotype (anti-Id) antibodies, and epitope-binding fragments of the antibodies, but is not limited thereto.

The "epitope" refers to a protein determinant to which an antibody specifically bind. Epitopes usually consist of chemically active surface groupings of molecules, for example, amino acids or sugar side chains, and usually have specific three dimensional structural characteristics, as well as specific charge characteristics. Conformational and non-conformational epitopes are distinguished in that the binding to the former but not the latter is lost in the presence of denaturing agents.

The antibody according to the present disclosure is characterized by specifically binding to srIκB, preferably by specifically binding to a site including the mutation sites (S32A and S36A) of srIκB.

In the present disclosure, the antibody or antigen-binding fragment is characterized by exhibiting a significantly higher binding affinity to srIκB than the wild-type IκB. Preferably, the antibody or antigen-binding fragment of the present disclosure is characterized by exhibiting about 1.1 times, about 1.2 times, about 1.3 times, about 1.4 times, about 1.5 times, about 1.6 times, about 1.7 times, about 1.8 times, about 1.9 times, or about 2.0 times or more, preferably, about 1.5 times or more, more preferably, about 2.0 time or more binding affinity to srIκB than the wild-type IκB. In the present disclosure, the antibody or antigen-binding fragment is characterized by binding to only srIκB without binding to the wild-type IκB.

"Humanized" forms of non-human (e.g., murine) antibodies are chimeric antibodies which include minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody), for example, mouse, rat, rabbit, or non-human primate having the desired specificity, affinity, and capacity. For humanization, residues in one or more framework domains (FRs) of the variable region of the recipient human antibody may be replaced with corresponding residues from the donor antibody of a non-human species. This helps to maintain the proper three-dimensional configuration of the grafted CDR(s), thereby improving affinity and antibody stability. Humanized antibodies may include new residues that are found neither in the recipient antibody nor in the donor antibody, for example, to further refine antibody performance.

The "human antibody" is a molecule derived from human immunoglobulin, meaning that the entire amino acid sequence constituting the antibody, including the complementarity determining region and structural region, is composed of human immunoglobulin.

"Chimeric" antibodies (immunoglobulins) in which a portion of the heavy and/or light chain is identical or homologous to corresponding sequences in antibodies derived from a particular species or belonging to a particular antibody class or subclass, while the remainder of the chain(s) is identical or homologous to corresponding sequences in antibodies derived from another species or belonging to another antibody class or subclass, as well as fragments of such antibodies exhibiting the desired biological activity are included.

As used herein, the "antibody variable region" or "antibody variable domain" refers to a portion of light chain and heavy chain of an antibody molecule, including amino acid sequences of complementarity determining region (CDR; i.e., CDR1, CDR2, and CDR3) and framework region (FR).

VH refers to the variable domain of the heavy chain. VL refers to the variable domain of the light chain.

The "complementarity determining region" (CDR; i.e., CDR1, CDR2, and CDR3) indicates the amino acid residue of an antibody variable domain, which is required for binding to an antigen. Each variable domain generally has 3 CDR regions that are identified as CDR1, CDR2, and CDR3.

Specifically, in the present disclosure, the antibody binding to srIκB or the antigen-binding fragment thereof may be characterized by including the heavy chain variable region including the heavy chain CDR1 of SEQ ID NO: 3, the heavy chain CDR2 of SEQ ID NO: 4, and the heavy chain CDR3 of SEQ ID NO: 5.

In the present disclosure, the antibody binding to srIκB or the antigen-binding fragment thereof may be characterized by including the light chain variable region including the light chain CDR1 of SEQ ID NO: 6, the light chain CDR2 of SEQ ID NO: 7, and the light chain CDR3 of SEQ ID NO: 8.

In the present disclosure, the antibody binding to srIκB or the antigen-binding fragment thereof may be characterized by including the heavy chain variable region including the heavy chain CDR1 of SEQ ID NO: 3, the heavy chain CDR2 of SEQ ID NO: 4, and the heavy chain CDR3 of SEQ ID NO: 5; and the light chain variable region including the light chain CDR1 of SEQ ID NO: 6, the light chain CDR2 of SEQ ID NO: 7, and the light chain CDR3 of SEQ ID NO: 8.

In the present disclosure, the antibody binding to srIκB or the antigen-binding fragment thereof may be characterized by including a heavy chain variable region selected from the group consisting of SEQ ID NO: 9 to SEQ ID NO: 14.

In the present disclosure, the antibody binding to srIκB or the antigen-binding fragment thereof may be characterized by including a light chain variable region selected from the group consisting of SEQ ID NO: 15 to SEQ ID NO: 29.

In the present disclosure, the antibody binding to srIκB or the antigen-binding fragment thereof may be characterized by including a heavy chain variable region selected from the group consisting of SEQ ID NO: 9 to SEQ ID NO: 14; and a light chain variable region selected from the group consisting of SEQ ID NO: 15 to SEQ ID NO: 29.

"Framework region" (FR) means a residue of variable domain other than CDR residue. Each variable domain generally has four FRs that are identified as FR1, FR2, FR3 and FR4.

"Fv" fragment is an antibody fragment which has a full antibody recognizing and binding site. This region is composed of a dimer in which one heavy chain variable domain and one light chain variable domain are, for example, actually covalently linked as scFv.

"Fab" fragment includes variable and constant domains of a light chain and a variable domain and the first constant domain (CH1) of a heavy chain. F(ab)₂ antibody fragment generally includes a pair of Fab fragments which are covalently linked, via hinge cysteine, near their carboxy terminals.

"Single chain Fv" or "scFv" antibody fragment includes VH and VL domains of an antibody, and those domains are present within a single polypeptide chain. Fv polypeptide may further include a polypeptide linker between the VH domain and VL domain so that scFv forms a desired structure for binding to an antigen.

The antibody binding to srIκB or the antigen-binding fragment thereof may include a heavy chain variable region including a sequence having about 90% or more sequence homology to an amino acid sequence of an antibody done of exemplary embodiment of the present disclosure. Further, the antibody binding to srIκB or the antigen-binding fragment thereof may include a light chain variable region including a sequence having about 90% or more sequence homology to an amino acid sequence of an antibody clone of exemplary embodiment of the present disclosure.

The antibody or antibody fragment of the present disclosure may include, within the scope of specifically recognizing srIκB, the sequence of the anti-srIκB antibody of the present disclosure described herein as well as biological equivalents thereof. For example, the amino acid sequence of the antibody may be additionally modified to further improve the binding affinity and/or other biological properties of the antibody. Such modifications include, for example, deletion, insertion, and/or substitution of the amino acid sequence residues of the antibody. Such amino acid variations are made based on the relative similarity of amino acid side chain substituents, e.g., hydrophobicity, hydrophilicity, charge, size, etc. By analysis of the size, shape, and type of amino acid side chain substituents, it is recognized that each of arginine, lysine and histidine is a positively charged residue; alanine, glycine and serine have similar sizes; and phenylalanine, tryptophan, and tyrosine have similar shapes. Based on these considerations, it is thus found that arginine, lysine and histidine; alanine, glycine, and serine; and phenylalanine, tryptophan, and tyrosine, respectively, are biologically functional equivalents.

Considering the mutation having the above-mentioned biological equivalent activity, the antibody of the present disclosure or the nucleic acid molecule encoding the same is interpreted to include a sequence showing substantial identity with the sequence described in the sequence listing. The substantial identity means a sequence showing at least 80% homology, preferably at least 90% homology, and most preferably at least 95% homology, 96% or more homology, 97% or more homology, 98% or more homology, or 99% or more homology by aligning the sequence of the present disclosure with any other sequence as much as possible and analyzing the aligned sequence using algorithms commonly used in the art.

Alignment methods for sequence comparison are well known in the art. NCBI Basic Local Alignment Search Tool (BLAST) may be accessible from NBCI, etc., and may be used in association with sequence analysis programs such as blastp, blasm, blastx, tblastn, and tblastx on the Internet. BLSAT is available at www.ncbi.nlm.nih.gov/BLAST/. A comparison of sequence homology using this program may be found at www.ncbi.nlm.nih.gov/BLAST/blast.help.html.

On the basis of this, the antibody or antibody fragment of the present disclosure may have 90%, 91%, 92%, 93%, 94%, 95%, 96%, 97%, 98%, 99%, or more homology to the specified sequence described herein or the entire sequence. Such homology may be determined by sequence comparison and/or alignment by a method known in the art. For example, the percent sequence homology of the nucleic acid or protein of the present disclosure may be determined using sequence comparison algorithms (i.e., BLAST or BLAST 2.0), manual alignment, visual inspection.

In the present disclosure, the antibody or antigen-binding fragment may be used after dilution.

In the present disclosure, the antibody or antigen-binding fragment may be diluted to about 1:100 or more, about 1:1,000 or more, about 1:5,000 or more, about 1:10,000 or more, about 1:50,000 or more, about 1:100,000 or more, or about 1:500,000 or more.

In the present disclosure, the antibody or antigen-binding fragment may be diluted at a concentration of about 1/100 to about 1/1,000,000, preferably at a concentration of 1/1,000 to about 1/500,000, more preferably at a concentration of 1/5,000 to about 1/500,000, more preferably at a concentration of 1/10,000 to about 1/500,000, more preferably at a concentration of 1/50,000 to about 1/500,000, and most preferably at a concentration of 1/100.000 to about 1/500,000.

Still another aspect of the present disclosure relates to a nucleic acid encoding the antibody or the antigen-binding fragment thereof.

By isolating the nucleic acid encoding the antibody of the present disclosure or the antigen-binding fragment thereof, the antibody or the antigen-binding fragment thereof may be produced by a recombination technique. The nucleic acid is isolated and inserted into a replicable vector, further cloned (DNA amplification) or further expressed.

On the basis of this, still another aspect of the present disclosure relates to a vector including the nucleic acid.

The "nucleic acid" has a meaning which broadly encompasses DNA (gDNA and cDNA) and RNA molecules, and nucleotide as a basic constitutional unit of nucleic acid includes not only a natural nucleotide but also an analogue having modified sugar or base moieties. The nucleic acid sequence encoding heavy chain and light chain variable regions of the present disclosure may be modified. The modification includes addition, deletion, or non-conservative or conservative substitution of a nucleotide.

DNA encoding the antibody may be easily isolated or synthesized by using a common process (e.g., by using an oligonucleotide probe capable of specifically binding to DNA encoding heavy and light chains of an antibody). Various vectors are available. As a vector component, one or more of the followings are generally included, but it is not limited thereto: signal sequence, replication origin, one or more marker genes, enhancer element, promoter, and transcription termination sequence.

As used herein, the term "vector" is a means for expressing a target gene in a host cell, and includes a plasmid vector; a cosmid vector; a bacteriophage vector; and a virus vector such as adenovirus vector, retrovirus vector, or adeno-associated virus. In the vector, a nucleic acid encoding the antibody is operably linked to a promoter.

"Operably linked" means a functional linkage between a nucleic acid expression control sequence (e.g., array on promoter, signal sequence, or transcription regulation factor binding site) and other nucleic acid sequence, and according to the linkage, transcription and/or translation of other nucleic acid sequence may be regulated by the control sequence.

When a prokaryotic cell is used as a host, a potent promoter enabling the progress of transcription (e.g., tac promoter, lac promoter, lacUV5 promoter, lpp promoter, pLλ promoter, pRλ promoter, rac5 promoter, amp promoter, recA promoter, SP6 promoter, trp promoter, T7 promoter, etc.), a ribosome binding site for initiation of translation, and a transcription/translation termination sequence are generally included. Moreover, when a eukaryotic cell is used as a host, a promoter derived from a genome of mammalian cells (e.g., metallothionine promoter, β-actin promoter, human hemoglobin promoter, and human muscle creatine promoter) or a promoter derived from mammalian virus (e.g., adenovirus late promoter, vaccinia virus 7.5K promoter, SV40 promoter, cytomegalo virus (CMV) promoter, tk promoter of HSV, mouse breast tumor virus (MMTV) promoter, LTR promoter of HIV, moloney virus promoter, Epstein-Barr virus (EBV) promoter, and Rous sarcoma virus (RSV) promoter) may be used. As a transcription termination sequence, a polyadenylated sequence is generally included.

Depending on a case, the vector may be fused to other sequence for easier purification of an antibody expressed therefrom. Examples of a sequence for fusion include glutathione S-transferase (Pharmacia, USA), maltose binding protein (NEB, USA), FLAG (IBI, USA), 6×His (hexahistidine; Qiagen. USA), etc.

The vector includes, as a selection marker, an antibiotics resistant gene generally used in the art, and examples thereof include a gene resistant to ampicillin, gentamycin, carbenicillin, chloramphenicol, streptomycin, kanamycin, geneticin, neomycin, or tetracycline.

Still another aspect of the present disclosure relates to a host cell into which the nucleic acid or vector of the present disclosure is introduced. The cell used for producing the antibody of the present disclosure may be a cell of a prokaryote, yeast, or a higher eukaryotic organism, but is not limited thereto.

The vector may be introduced into the host cell by a method such as transformation, transfection, etc. As used herein, the term "transformation" refers to introducing DNA into a host cell so that the DNA is replicable, either as an extrachromosomal element, or by chromosomal integration. As used herein, the term "transfection" refers to the taking up of an expression vector by a host cell, whether or not any coding sequences are in fact expressed. For introduction of the vector, various kinds of generally used techniques such as electrophoresis, calcium phosphate precipitation, DEAE-dextran transfection, lipofection, etc., may be used to introduce an exogenous nucleic acid (DNA or RNA) into a prokaryotic or eukaryotic host cell, but are not limited thereto.

It should be understood that not all vectors and expression control sequences will function equally well to express the DNA sequences of the present disclosure. Neither will all hosts function equally well with the same expression system. However, one of skill in the art may make a selection among various vectors, expression control sequences, and hosts without undue experimentation and without departing from the scope of the present disclosure. For example, in selecting a vector, the host must be considered because the vector must replicate therein. The vector's copy number, the ability to control that copy number, and the expression of any other proteins encoded by the vector, such as antibiotic markers, should also be considered. In selecting an expression control sequence, a variety of factors should also be considered. These include, for example, the relative strength of the sequence, its controllability, and its compatibility with the DNA sequence of the present disclosure, particularly as regards potential secondary structures. Unicellular hosts should be selected by consideration of the chosen vector, toxicity of the product encoded by the DNA sequences of the present disclosure, secretion characteristics, ability to correctly fold proteins, culture and fermentation requirements, and the ease of purification of the product encoded by the DNA sequence of the present disclosure from the host. Within these parameters, one of skill in the art may select various vectors/expression control sequences/host combinations that are able to express the DNA sequence of the present disclosure on fermentation or large-scale animal culture. In cloning cDNA by the expression cloning, screening procedures such as a binding method, a panning method, and a film emulsion method may be applied.

Prokaryotic host cells may be used, such as *Escherichia coli*, and strains of the genus *Bacillus* such as *Bacillus*

*subtilis* and *Bacillus thuringiensis, Streptomyces, Pseudomonas* (e.g., *Pseudomonas putida*), *Proteus mirabilis*, and *Staphylococcus* (e.g., *Staphylococcus carnosus*).

However, animal cells currently receive the highest attention. Examples of the useful host cell line may include COS-7, BHK, CHO, CHOK1, DXB-11, DG-44, CHO/-DHFR, CV1, COS-7, HEK293, BHK, TM4, VERO, HELA, MDCK, BRL 3A, W138, Hep G2, SK-Hep, MMT, TRI, MRC 5, FS4, 3T3, RIN, A549, PC12, K562, PER.C6, SP2/0, NS-0, U20S, or HT1080, but are not limited thereto.

In the present disclosure, the nucleic acid encoding the anti-srIκB antibody or antigen-binding fragment thereof may be directly introduced into the genome of a host cell and may exist as a chromosomal factor. To those skilled in the art to which the present disclosure pertains, it will be apparent that even though the gene is inserted into the genomic chromosome of the host cell, it will have the same effect as when the recombinant vector is introduced into the host cell.

Still another aspect of the present disclosure relates to a method of preparing the antibody binding to srIκB or the antigen-binding fragment thereof, the method including the steps of (a) culturing the host cells; and (b) collecting the antibody or the antigen-binding fragment thereof from the cultured host cells.

The cells may be cultured in various media, and commercially available media may be used without limitation as the culture media. All other essential supplements known to those of ordinary skill in the art may be included at appropriate concentrations. Culture conditions, for example, temperature, pH, etc., have already been used for expression in the selected host cell, and will be apparent to those of ordinary skill in the art.

Collecting of the antibody or antigen-binding fragment thereof may be performed by, for example, removing impurities by centrifugation or ultrafiltration, and purifying the resulting product by, for example, affinity chromatography. Additional other purification techniques, for example, anion or cation exchange chromatography, hydrophobic interaction chromatography, or hydroxylapatite chromatography may be used.

Still another aspect of the present disclosure relates to a composition for sensing, detecting, purifying, or targeting srIκB protein, and/or identifying activity thereof, the composition including the anti-srIκB antibody of the present disclosure or the antigen-binding fragment thereof.

Various methods of sensing, detecting, purifying, or targeting a target, or identifying activity thereof using an antibody specifically binding to the target are known in the art, and those skilled in the art may perform the sensing, detecting, purifying, or targeting of the srIκB protein, and/or identifying of the activity thereof by using the composition including the anti-srIκB antibody of the present disclosure or the antigen-binding fragment thereof.

As used herein, the "sensing" or "detecting" means finding srIκB in a sample for sensing or detecting srIκB. or examining whether srIκB is present.

In the present disclosure, the sensing or detecting may be performed by using a colorimetric method, an electrochemical method, a fluorometric method, luminometry, a particle counting method, absorbance measurement, a spectrometric method, a Raman spectroscopic method, a surface plasmon resonance method, an interferometric method, visual assessment, a scintillation counting method, etc., but is not limited thereto.

In the present disclosure, various labels may be used for sensing and detecting the target srIκB. For example, the labels may include a dye, an enzyme, a fluorescent substance, a ligand, a luminescent substance, a microparticle, a radioactive isotope, a metal nanoparticle, a lanthanide element, a Raman reporter, an electrochemical tag, a magnetic particle, etc., but are not limited thereto. In addition, the sensing or detecting is also possible in a label-free manner without using a label. For example, it may be surface plasmon resonance, isothermal titration calorimetry, biolayer interferometry, etc., but is not limited thereto.

As used herein, the "purifying" means isolating pure or substantially pure srIκB from a mixture containing various substances or impurities in addition to the srIκB. In particular, the anti-srIκB antibody of the present disclosure may be characterized by specifically purifying only srIκB from a mixture containing both srIκB and the wild-type IκB.

As used herein, the "targeting" means that a material non-specific to a target is allowed to be target-specific. A material non-specific to srIκB may be targeted by binding or conjugating it with the anti-srIκB antibody of the present disclosure or the antigen-binding fragment. The material non-specific to srIκB may be a material specific to a target other than srIκB.

As used herein, the "identifying activity" means detecting or quantifying the activity of srIκB. For example, the NF-κB inhibitory activity of srIκB, inactivation by a proteasome, etc. may be detected, but is not limited thereto.

In the present disclosure, the composition may be used not only to identify the activity, but also to control the activity of srIκB.

In the present disclosure, the antibody or antigen-binding fragment thereof may be included in the composition after dilution.

In the present disclosure, the antibody or antigen-binding fragment thereof may be diluted to about 1:100 or more, about 1:1,000 or more, about 1:5,000 or more, about 1:10,000 or more, about 1:50,000 or more, about 1:100,000 or more, or about 1:500,000 or more.

In the present disclosure, the antibody or antigen-binding fragment thereof may be diluted at a concentration of about 1/100 to about 1/1,000,000, preferably at a concentration of 1/1,000 to about 1/500,000, more preferably at a concentration of 1/5,000 to about 1/500,000, much more preferably at a concentration of 1/10,000 to about 1/500,000, still much more preferably at a concentration of 1/50,000 to about 1/500,000, and most preferably at a concentration of 1/100,000 to about 1/500,000.

Still another aspect of the present disclosure relates to use of the anti-srIκB antibody of the present disclosure or the antigen-binding fragment thereof in sensing, detecting, purifying, or targeting the srIκB protein, and/or identifying activity thereof.

In the present disclosure, the anti-srIκB antibody or the antigen-binding fragment thereof may be used for sensing, detecting, purifying, or targeting the srIκB protein, and identifying activity thereof, but is not limited thereto. Any use that may be recognized by a person skilled in the art that it may be achieved by using the antibody of the present disclosure may be used without limitation.

Still another aspect of the present disclosure relates to use of the anti-srIκB antibody of the present disclosure or the antigen-binding fragment thereof in preparing the composition for sensing, detecting, purifying, or targeting the srIκB protein, and/or identifying activity thereof.

In another aspect, the present disclosure relates to a multi-specific antibody including the antibody or the antigen-binding fragment thereof. The multi-specific antibody may include a tetra-specific antibody, a tri-specific antibody, or a bi-specific antibody. For example, the bi-specific antibody refers to an antibody capable of binding to two different types of antigens (target proteins), and is in a form prepared by genetic engineering or any method.

The multi-specific antibody refers to an antibody having binding specificity to two or more different types of antigens. Antibodies belonging to the multi-specific antibody may be classified into scFv-based antibodies, Fab-based antibodies, and IgG-based antibodies, etc. In the case of the bi-specific antibody, since it is able to inhibit or amplify two signals at the same time, it may be more effective than the case of inhibiting/amplifying one signal. Compared with the case where each signal is treated with each signal inhibitor, a low-dose administration is possible, and two signals may be inhibited/amplified at the same time and space.

Methods of preparing bi-specific antibodies are widely known. Traditionally, recombination production of bi-specific antibodies is based on the co-expression of two immunoglobulin heavy chain/light chain pairs under conditions in which the two heavy chains have different specificities.

In the case of a bi-specific antibody based on an scFv, a hybrid scFv may be prepared in the form of a heterodimer by combining VL and VH of different scFvs with each other to make a diabody, and different scFvs may be linked to each other to make a tandem ScFv, and a heterodimeric miniantibody may be prepared by expressing CH1 and CL of Fab at the ends of each scFv, and a heterodimeric scFv-type minibody may be prepared by substituting some amino acids of CH3 domain, which is the homodimeric domain of Fc, to change to a heterodimer structure in the "knob into hole" form, and expressing these altered CH3 domains at different scFv ends.

In the case of a bi-specific antibody based on Fab, a heterodimeric Fab may be prepared by combining individual Fab's directed against a specific antigen with each other using a disulfide bond or a mediator, and the antigen valency may be doubled by expressing scFvs for different antigens at the ends of heavy or light chains of a specific Fab, or it may be prepared to have four antigen valencies in the form of homodimers by providing a hinge region between Fab and scFv. In addition, a dual-targeted bibody with three antigen valency may be prepared by fusing scFvs for different antigens to light and heavy chain ends of Fab, and a triple-targeted bibody with three antigen valency may be prepared by fusing different scFvs to light and heavy chain ends of Fab, and it may also be obtained by chemically conjugating three different Fabs.

In the case of a bi-specific antibody based on IgG, a method of producing a bi-specific antibody by recrossing mouse and rat hybridomas (Trion Pharma) to produce a hybrid hybridoma (also known as quadromas) is known. In addition, it is also possible to prepare a bi-specific antibody in the so-called "Holes and Knob" form, which is made in the heterodimeric form by modifying some amino acids of the CH3 homodimeric domain of Fc with respect to different heavy chains while sharing the light chain portion. In addition to the bi-specific antibody in the heterodimeric form, (scFv)4-IgG in a homodimeric form may also be prepared by fusion-expressing two different scFvs in constant domains instead of variable domains of light and heavy chains of IgG.

EXAMPLE

Hereinafter, the present invention will be described in more detail with reference to Examples. However, these Examples are for illustrative purposes only, and it is apparent to those skilled in the art that the scope of the present invention is not intended to be limited by these Examples.

Example 1. Determination of Target Antigen for Screening

Figure 2:
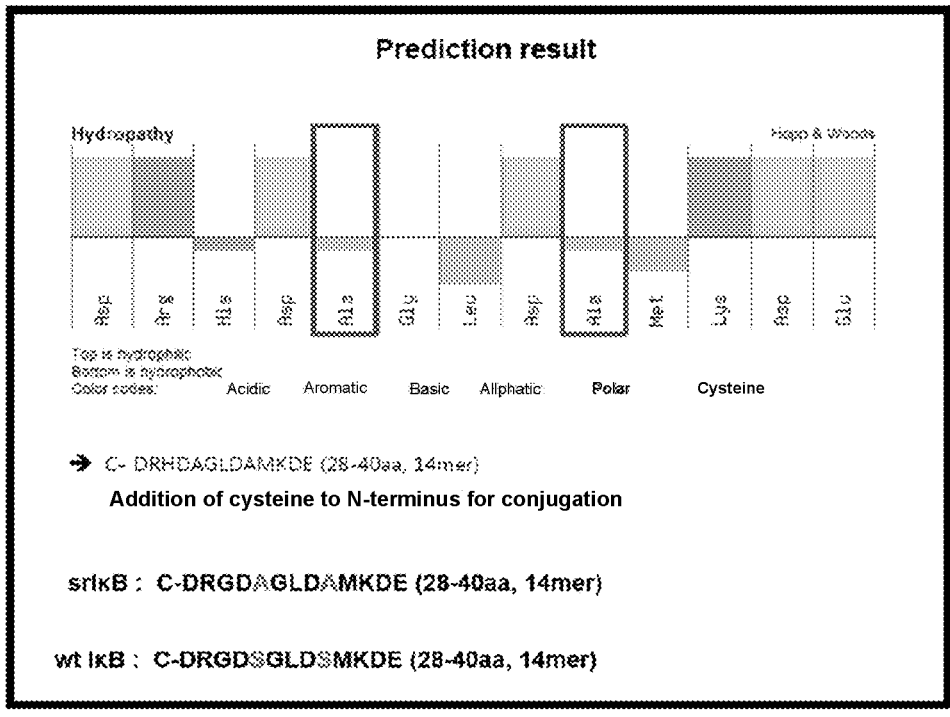
FIG. 2 shows characteristics of the amino acid sequence of a partial peptide (the red box of FIG. 1) of srIκB which includes a mutation site used for screening, in which cysteine was added to the N-terminus of each peptide (WT IκB and srIκB) for conjugation.

In the antibody screening, a target antigen was srIκB, and proteins used for screening were stored at −80° C. An amino acid sequence of SrIκB is as shown in the right of FIG. 1. However, as compared with an amino acid sequence of the wild-type IκB (left of FIG. 1), srIκB is a mutant, in which each serine (S) at positions 32 and 36 was substituted with alanine (A), and has the same amino acid sequence, except for the two amino acids. Therefore, for screening of an antibody specifically binding to srIκB while not binding to the wild-type IκB, a peptide (amino acids at positions 28 to 40) including the mutation site was determined as the target antigen for the srIκB antibody screening, and the peptide of the wild-type IκB corresponding thereto was used for negative screening (FIG. 2). Partial peptides of srIκB and wild-type IκB used for screening are as described in Table 1.

TABLE 1

| Amino acid sequences of peptides used for screening | |
|---|---|
| Name | Amino acid sequence (N' to C') |
| WtIκB (14 mer) | C-DRHDSGLDSMKDE (SEQ ID NO: 1) |
| srIκB (14 mer) | C-DRHDAGLDAMKDE (SEQ ID NO: 2) |

"C-" indicates cysteine added to the N-terminus of the peptide for conjugation.
Amino acids in bold and underlined indicate mutation sites (S32A, S36A).

Example 2: Preparation of Polyclonal Antibody

Figure 3:
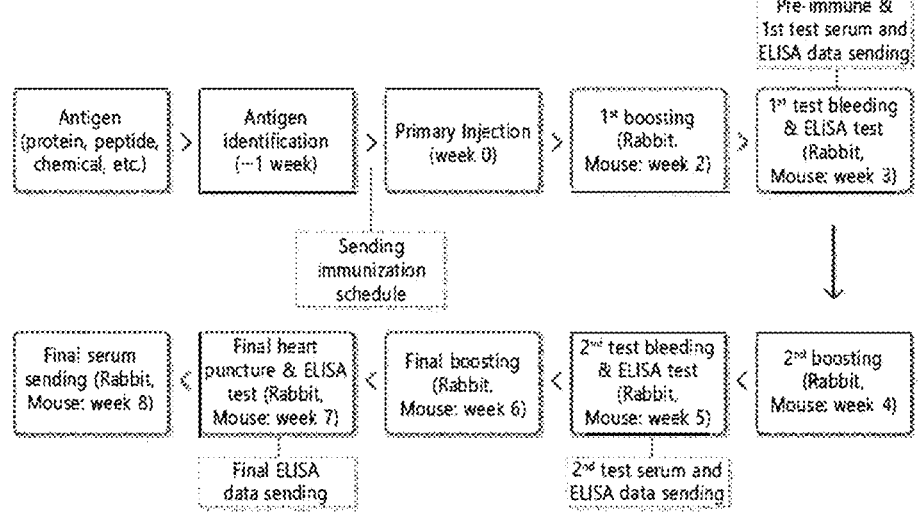
FIG. 3 shows a schematic illustration of the preparation of a polyclonal antibody by Abclon, Inc.

A polyclonal antibody specifically recognizing the mutant, in which each serine (S) at positions 32 and 36 was substituted with alanine (A), as described in Table 1, was prepared by the following method. Production of polyclonal antisera 1st boosted antibody production by subcutaneously injecting the srIκB peptide used for the screening as an antigen into rabbits, in which a preliminary immune response (week 0) was induced for 4 weeks (week 4, 1st boosting). 2 weeks after induction of the immune response for the 1st antibody production, 2nd antibody production was boosted (500 μg/rabbit; 6 weeks, 2nd boosting), and 2 weeks later, 3rd antibody production was boosted (500 μg/rabbit; week 8, 3rd boosting). One week later, sera were obtained by cardiac puncture to obtain anti-srIκB polyclonal antisera, and secondary purification was performed by affinity chromatography using a peptide against the target antigen to obtain a rabbit anti-srIκB polyclonal antibody (FIG. 3).

Example 2-1: Examination of Immune Effect of Anti-srIκB Antibody

To examine the immune effect of the anti-srIκB antibody in the serum obtained from the rabbit, enzyme-linked immunosorbent assay (ELISA) was performed by the following method.

In detail, the antigen was diluted to 2 μg/mL with a coating buffer, and 50 μL thereof was dispensed into each well, and left at 4° C. overnight or at 37° C. for 3 hours for coating. Thereafter, the coating solution was discarded and 250 μL of 2% skim milk/TBST solution was dispensed, followed by blocking at 37° C. for one hour. One hour later, each well was washed with TBST solution, and 100 μL of a primary antibody was dispensed into each well and allowed to react at 37° C. for two hours. Thereafter, after washing three times with TBST, 50 μL of a secondary antibody diluted at 1:5000 was dispensed into each well and allowed to react at 37° C. for 1 hour. After washing with TBST five times, 50 μL of a color developing solution was dispensed into each well. When the color changed, a stop solution was added to stop the reaction, and then the O.D. value was measured at 495 nm. As a result, it was confirmed that the anti-srIκB antibody had the immune effect. (FIG. 4)

Example 2-2: Examination of Specificity of Anti-srIκB Antibody

To load the target protein fused with srIκB-mCherry, the corresponding construct was transformed into an exosome-producing cell line (HEK293T), and both the produced exosome and the introduced cell line were prepared for Western blotting. The cell and exosome pellets were obtained through centrifugation, and for Western blotting, the protein was extracted using RIPA buffer, and the extracted protein was quantified, and boiled with 2× sample buffer, and subjected to SDS-PAGE. Thereafter, the gel was transferred to a PVDF membrane, and srIκB protein was detected using the isolated and purified polyclonal antibody (FIG. 5).

Example 3: Screening and Selection of Monoclonal Antibody

Example 3-1: Antibody Screening Through ELISA

A monoclonal antibody against srIκB was prepared according to Abclon's Abclon-MANI protocol (FIG. 6). First, the antibody was first screened through a fusion screening method (ELISA), and the screening conditions are as shown in Table 2. As a result of ELISA, clones binding to srIκB were selected, based on clones with an O.D. value of 0.5 or more.

TABLE 2

| 1st screening (ELISA) conditions | | | |
|---|---|---|---|
| ELISA reader | PerkinElmer Victor X3 | Antigen coating | 100 ng/well |
| Measurement filter | 450 nm | Primary antibody (Mouse IgG-HRP) | 1:10,000 dilution |
| Measurement mode | Single Point Photo | Substrate | TMB |

Thereafter, the selected clones were transferred to a 24-well plate, and binding was reconfirmed through ELISA for srIκB peptide, WT IκB peptide, Lysate, and SMCC control using ELISA under the same conditions. Six clones (2F8, 5A2, 6B5, 6C10, 9H8, and 9E10) showing an O.D. value of 0.5 or more and specifically binding to the srIκB peptide antigen were selected (FIG. 8).

Example 3-2: Antibody Screening Through Western Blotting

As shown in FIG. 9, six antibody clones specific to the srIκB peptide, which were selected through ELISA, were compared with the positive control through Western blotting, and bands of the desired size were found in three clones of 5A2, 6C10, and 9H8. The Western blotting conditions are shown in Table 3 below.

TABLE 3

| Screening (WB) conditions | | | |
|---|---|---|---|
| SDS-PAGE gel (%) | 10% | Loading sample | 500 μg of Ag/strip |
| Primary antibody | 800 μL of Hybridoma culture supernatant stock | Secondary antibody (Mouse IgG-HRP) | 1:5,000 dilution |
| Substrate | AbSignal | Exposure time | 50 seconds |

Example 3-3: Antibody Screening Through Immunoprecipitation (IP)

In order to more clearly confirm the results of screening for the six antibody clones specific to the srIκB peptide, which were selected through ELISA, IP was performed using the cell culture supernatant of the cell line producing the srIκB-loaded exosome. The IP was performed under conditions shown in Table 4 below. In the IP experiment, bands of the desired size were found in three clones of 2F8, 6C10, and 9H8 (FIG. 10).

TABLE 4

| Screening (IP) conditions | | | |
|---|---|---|---|
| SDS-PAGE gel (%) | 10% | Loading sample | 500 μg of Ag/strip |
| Primary antibody | Mouse final serum #2 1:2000 | Secondary antibody (Mouse IgG-HRP) | 1:2,000 dilution |
| Substrate | AbSignal | Exposure time | 120 seconds |

Example 4: Single Cell Cloning of Selected Antibody

Two clones (6C10, 9H8) positive in all of ELISA, WB, and IP in the screening of Example 3 were subjected to single cell cloning, and another two clones (2F8, 5A2) showing a band in either IP or WB were also cloned together.

Example 5: ELISA and Isotype Screening of Final Stored Clones

The clones (2F8, 5A2, 6C10, and 9H8) finally stored through cloning were ultimately subjected to ELISA and Isotype Screening. ELISA was performed using, as an antigen, the cells producing srIκB-loaded exosomes, and the conditions for ELISA are shown in Table 2. It was confirmed that all of the four clones reacted with the antigen. In addition, for isotype screening of the four selected clones, the isotypes were examined using the culture supernatant of the cells producing srIκB-loaded exosomes. The conditions for performing the isotype screening are shown in Table 5 below.

TABLE

| Isotype screening conditions | | | |
|---|---|---|---|
| ELISA reader | PerkinElmer Victor X3 | | |
| Measurement filter | 450 nm | | |
| Measurement mode | Single Point Photo | Substrate | TMB |

As a result of ELISA, it was confirmed that all of the stored clones reacted with srIκB, as shown in FIG. 11. As a result of isotype screening, specific isotypes of individual clones were confirmed to have the highest binding affinity, as shown in FIG. 12: IgG1/kappa of 2F8 done, IgG2a/kappa of 6C10 and 9H8 clones, IgG2b/kappa of 5A2 clone.

Example 6: Preparation of Hybridoma Cell Line (Anti-srIκB Antibody)

After the final screening, a hybridoma cell line for each of the selected clones was prepared (FIG. 7). As the antigen, the srIκB protein used in each screening was used.

The srIκB antigen was mixed with an adjuvant (sigma), and the mixture was injected into mice (BALB/c), and the blood was collected from mice to examine antibody production by ELISA. After performing immunization twice, the antibody titer (1:5,000) appropriately increased, and the spleen was removed from the immunized mice to isolate B lymphocytes, which were then fused with cultured myeloma cells (sp2/0). The fused cells were cultured in a medium (HAT medium) to which hypoxanthin, aminopterine, and thymidine were added, and only cells (hybridoma) fused with myeloma and B lymphocytes were selectively selected and cultured (because B lymphocytes are normal cells, they die when cultured for a long period of time, whereas myeloma cells are the introduced cells, and thus they are eliminated by HAT selection).

Among the obtained hybridoma cells, cells producing antibodies reacting with the antigen were identified using ELISA, and a process (cloning) of separating positive cells and negative cells using a limiting dilution method for positive cells was repeated to produce monoclonal cells (hybridoma) producing antigen-responsive antibodies. The resulting final hybridoma cell line products are shown in Table 6 below.

TABLE 6

| Hybridoma cell line (Anti-srIκB antibody) final product Final product: Hybridoma cell line (anti-srIκB antibody) | | | |
|---|---|---|---|
| Clone | 2F8, 5A2, 6C10, 9H8 | Freezing vial | 5 vials per clone |
| Culture media | 10% FBS/DMEM | Culture condition | 37° C., 5% CO$_2$ |

Example 7: Ascites Purification of srIκB Antibody and Test

Ascites purification was performed for the two clones (2F8, 5A2) ultimately selected.

Pristane was injected into 10-week-old BALB/c mice, and hybridoma cells were cultured, and IP injection thereof into the abdominal cavity of mice was performed. 1 week to 2 weeks after injection, when ascites were generated, ascites were collected from the abdominal cavity and centrifuged at 3000 rpm for 15 minutes to obtain a supernatant. The titer thereof was examined by ELISA, and tested by SDS-PAGE.

SDS-PAGE analysis was performed using ascites for each obtained clone.

SDS-PAGE conditions are as shown in Table 7 below. In each lane, a marker, control (BGG), and ascites dilutions of each clone (undiluted, 1:2, 1:4, and 1:8) were loaded.

TABLE 7

| SDS-PAGE gel (%) | 12% | Antibody size | 50 kDa, 25 kDa |
|---|---|---|---|

The obtained ascites were diluted 1:100, 1:1000, 1:5000, 1:10000, 1:50000, 1:100000 and 1:500000, and the titer was examined by ELISA under the same conditions as in Table 2. As a result, an O.D. value of 1.0 or more was recorded even at a high dilution rate (FIG. 13).

An antibody test was performed by Western blotting using the culture supernatant of the hybridoma cell line thus selected, and as a result, it was confirmed to specifically bind to the srIκB protein, as shown in FIG. 14. 2F8 and 5A2 monoclonal antibodies, which are the two clones ultimately selected, were used to compare their srIκB binding capacity in cells producing srIκB-loaded exosome and exosomes. As a result, it was ultimately confirmed that 2F8 was more specific, as shown in FIG. 15.

Example 8: Sequence Analysis of srIκB Antibody Ultimately Selected

Sequence analysis was performed on the hybridoma expressing 2F8, which is the srIκB antibody ultimately selected in Example 7. As a result, the hybridoma producing the 2F8 antibody was confirmed to include the same heavy chain and light chain CDRs, as shown in Tables 8 and 9 below.

TABLE 8

| Heavy chain/light chain CDR sequences of 2F8 antibody | | | |
|---|---|---|---|
| Anti-srIκB antibody (2F8) | | Amino acid sequence | SEQ ID NO: |
| Heavy chain | CDR1 | GYSMS | 3 |
| | CDR2 | YISSYYYSTYYADSVKG | 4 |
| | CDR3 | YGYSGYFDY | 5 |
| light chain | CDR1 | RASKSVSTSGYSYMH | 6 |
| | CDR2 | LVSNLES | 7 |
| | CDR3 | QHIRELT | 8 |

TABLE 9

| | Amino acid sequences of heavy chain and light chain variable regions of sequenced hybridoma and Primer sequences used | |
|---|---|---|
| Hybridoma No. | Amino acid sequence | SEQ ID NO |
| H2-VH | EVQVVESGGGLVQPGGSLRLSCAASGFTFSGYSMSW VRQAPGKGLEWVSYISSYYYSTYYADSVKGRFTISR DNSKNTLYLQMNSLRAEDTAVYYCARYGYSGYFDY WGQGTPVTVSA | 9 |
| H4-VH | EVQRVESGGGLVQPGGSLRLSCAASGFTFSGYSMSW VRQAPGKGLEWVSYISSYYYSTYYADSVKGRFTISR DNSKNTLYLQMNSLRAEDTAVYYCARYGYSGYFDY WGQGTPVTVSS | 10 |
| H5-VH | EVQLVESGGGLVQPGGSLRLSCAASGFTFSGYSMSW VRQAPGKGLEWVSYISSYYYSTYYADSVKGRFTISR DNSKNTLYLQMNSLRAEDTAVYYCARYGYSGYFDY WGQGTLVTVSS | 11 |
| H10-VH | EVQLVESGGGLVQPGGSLRLSCAASGFTFSGYSMSW VRQAPGKGLEWVSYISSYYYSTYYADSVKGRFTISR DNSKNTLYLQMNSLRAEDTAVYYCARYGYSGYFDY WGQGTPVTVSS | 12 |
| H19-VH | EVQVVESGGGLVQPGGSLRLSCAASGFTFSGYSMSW VRQAPGKGLEWVSYISSYYYSTYYADSVKGRFTISR DNSKNTLYLQMNSLRAEDTAVYYCARYGYSGYFDY WGQGTTVTVSS | 13 |
| H23-VH | EVQVVESGGGLVQPGGSLRLSCAASGFTFSGYSMSW VRQAPGKGLEWVSYISSYYYSTYYADSVKGRFTISR DNSKNTLYLQMNSLRAEDTAVYYCARYGYSGYFDY WGQGTTVTVSS | 14 |
| L1-VL | DVLMTQTPASLAVSLGQRATISYRASKSVSTSGYSY MHWNQQGPGQPPRLLIYLVSNLESGVPARFSGSGSG TDFTLNIHPVEEEDAATYYCQHIRELTRSEGGPSWS | 15 |
| L3-VL | DIQMTQSPASLAVSLGQRATISYRASKSVSTSGYSYM HWNQQKPGQPPRLLIYLVSNLESGVPARFSGSGSGT DFTLNIHPVEEEDAATYYCQHIRELTRSEGGPSWS | 16 |
| L4-VL | DIQMTWSPASLAVSLGQRATISYRASKSVSTSGYSYM HWNWQKPGWPPRLLIYLVSNLESGVPARFSGSGSGT DFTLNIHPVEEEDAATYYCQHIRELTRSEGGPSWS | 17 |
| L5-VL | DIKMTQSPASLAVSLGQRATISYRASKSVSTSGYSYM HWNQQKPGQPPRLLIYLVSNLEPGVPARFSGSGSGT DFTLNIHPVEEEDAATYYCQHIRELTRSEGGQSWK | 18 |
| L7-VL | DIVMTQSPASLAVSLGQRATISYRASKSVSTSGYSYM HWNQQKPGQPPRLLIYLVSNLESGVPARFSGSGSGT DFTLNIHPVEEEDAATYYCQHIRELTRSEGGPS | 19 |
| L8-VL | DIQMTQSPASLAVSLGQRATISYRASKSVSTSGYSYM HWNQQKPGQPPRLLIYLVSNLESGVPARFSGSGSGT DFTLNIHPVEEEDAATYYCQHIRELTRSEGGPSWS | 20 |
| L9-VL | DIKMNQSPASLVSLGQRATISYRASKSVSTSGYSYM HWNQQKPGQPPRLLIYLVSNLESGVPARFSGSGSGT DFTLNIHPVEEEDAATYYCQHIRELTRSEGGPSWS | 21 |
| L11-VL | DIVMTQAPASLAVSLGQRATISYRASKSVSTSGYSYM HWNQQKPGQPPRLLIYLVSNLESGVPARFSGSGSGT DFTLNIHPVEEEDAATYYCQHIRELTRSEGGPSWT | 22 |
| L12-VL | DIVMTQSPASLAVSLGQRATISYRASKSVSTSGYSYM HWNQQKPGQPPRLLIYLVSNLESGVPARFSGSGSGT DFTLNIHPVEEEDAATYYCQHIRELTRSEGGPSWS | 23 |
| L12-VL | DIQMTQSPASLAVSLGQRATISYRASKSVSTSGYSYM HWNQQKPGQPPRLLIYLVSNLESGVPARFSGSGSGT DFTLNIHPVEEEDAATYYCQHIRELTRSEGTKLE | 24 |
| L14-VL | DIVLTQSPASLAVSLGQRATISYRASKSVSTSGYSYM HWNQQKPGQPPRLLIYLVSNLESGVPARFSGSGSGT DFTLNIHPVEEEDAATYYCQHIRELTRSEGGPSWS | 25 |

TABLE 9-continued

| Amino acid sequences of heavy chain and light chain variable regions of sequenced hybridoma and Primer sequences used | | |
|---|---|---|
| Hybridoma No. | Amino acid sequence | SEQ ID NO |
| L15-VL | DIVMTQSPASLAVSLGQRATISYRASKSVSTSGYSYM HWNQQKPGQPPRLLIYLVSNLESGVPARKSGSGSGT DFTLNIHPVEEEDAATYYCQHIRELTRSEGGQSWK | 26 |
| L16-VL | DIVMTQSPASLAVSLGQRATISYRASKSVSTSGYSYM HWNQQKPGQPPRLLIYLVSNLESGVPARFSGSGSGT DFTLNIHPVEEEDAATYYCQHIRELTRSEGGPSWS | 27 |
| L18-VL | DILMTQSPASLAVSLGQRATISYRASKSVSTSGYSYM HWNQQKPGQPPRLLIYLVSNLESGVPARFSGSGSGT DFTLNIHPVEEEDAATYYCQHIRELTRSEGGPNWK | 28 |
| L19-VL | DILMTQSPASLAVSLGQRATISYRASKSYSTSGYSYM HWNQQKPGQPPRLLIYLVSNLESGVPARFSGSGSGT DFTLNIHPVEEEDAATYYCQHIRELTRSEGGPS | 29 |

*Those underlined indicate heavy chain/light chain CDR sequences

Primers used for sequence analysis of heavy chain or light chain of hybridoma are shown in Table 10 below.

TABLE 10

| Primers used in sequencing of heavy and light chains of hybridoma | | |
|---|---|---|
| Primer | Amino acid sequence | SEQ ID NO |
| Light chain (VL): forward primer | | |
| MSCVK-1 | GGGCCCAGGCGGCCGAGCTCGAYATCCAGCTGACTCAGCC | 30 |
| MSCVK-2 | GGGCCCAGGCGGCCGAGCTCGAYATTGTTCTCWCCCAGTC | 31 |
| MSCVK-3 | GGGCCCAGGCGGCCGAGCTCGAYATTGTGMTMACTCAGTC | 32 |
| MSCVK-4 | GGGCCCAGGCGGCCGAGCTCGAYATTGTGYTRACACAGTC | 33 |
| MSCVK-5 | GGGCCCAGGCGGCCGAGCTCGAYATTGTRATGACMCAGTC | 34 |
| MSCVK-6 | GGGCCCAGGCGGCCGAGCTCGAYATTMAGATRAMCCAGTC | 35 |
| MSCVK-7 | GGGCCCAGGCGGCCGAGCTCGAYATTCAGATGAYDCAGTC | 36 |
| MSCVK-8 | GGGCCCAGGCGGCCGAGCTCGAYATYCAGATGACACAGAC | 37 |
| MSCVK-9 | GGGCCCAGGCGGCCGAGCTCGAYATTGTTCTCAWCCAGTC | 38 |
| MSCVK-10 | GGGCCCAGGCGGCCGAGCTCGAYATTGWGCTSACCCAATC | 39 |
| MSCVK-11 | GGGCCCAGGCGGCCGAGCTCGAYATTSTRATGACCCARTC | 40 |
| MSCVK-12 | GGGCCCAGGCGGCCGAGCTCGAYRTTGTGATGACCCARAC | 41 |
| MSCVK-13 | GGGCCCAGGCGGCCGAGCTCGAYATTGTGATGACBCAGKC | 42 |
| MSCVK-14 | GGGCCCAGGCGGCCGAGCTCGAYATTGTGATAACYCAGGA | 43 |
| MSCVK-15 | GGGCCCAGGCGGCCGAGCTCGAYATTGTGATGACCCAGWT | 44 |
| MSCVK-16 | GGGCCCAGGCGGCCGAGCTCGAYATTGTGATGACACAACC | 45 |
| MSCVK-17 | GGGCCCAGGCGGCCGAGCTCGAYATTTTGCTGACTCAGTC | 46 |
| Light chain (VL): reverse primer | | |
| MHybJK12-B | AGATGGTGCAGCCACAGTTCGTTTKATTTCCAGYTTGGTCCC | 47 |
| MHybJK4-B | AGATGGTGCAGCCACAGTTCGTTTTATTTCCAACTTTGTCCC | 48 |
| MHybJK5-B | AGATGGTGCAGCCACAGTTCGTTTCAGCTCCAGCTTGGTCCC | 49 |

TABLE 10-continued

Primers used in sequencing of heavy and light chains of hybridoma

| Primer | Amino acid sequence | SEQ ID NO |
|--------|---------------------|-----------|
| Heavy chain (VH): forward primer | | |
| MHyVH1 | GCTGCCCAACCAGCCATGGCCCTCGAGGTRMAGCTTCAGGAGTC | 50 |
| MHyVH2 | GCTGCCCAACCAGCCATGGCCCTCGAGGTBCAGCTBCAGCAGTC | 51 |
| MHyVH3 | GCTGCCCAACCAGCCATGGCCCTCGAGGTGCAGCTGAAGSASTC | 52 |
| MHyVH4 | GCTGCCCAACCAGCCATGGCCCTCGAGGTCCARCTGCAACARTC | 53 |
| MHyVH5 | GCTGCCCAACCAGCCATGGCCCTCGAGGTBCAGCTBCAGCARTC | 54 |
| MHyVH6 | GCTGCCCAACCAGCCATGGCCCTCGAGGTYCARCTGCAGCAGTC | 55 |
| MHyVH7 | GCTGCCCAACCAGCCATGGCCCTCGAGGTCCACGTGAAGCAGTC | 56 |
| MHyVH8 | GCTGCCCAACCAGCCATGGCCCTCGAGGTGAASSTGGTGGAATC | 57 |
| MHyVH9 | GCTGCCCAACCAGCCATGGCCCTCGAGGTGAWGYTGGTGGAGTC | 58 |
| MHyVH10 | GCTGCCCAACCAGCCATGGCCCTCGAGGTGCAGSKGGTGGAGTC | 59 |
| MHyVH11 | GCTGCCCAACCAGCCATGGCCCTCGAGGTGCAMCTGGTGGAGTC | 60 |
| MHyVH12 | GCTGCCCAACCAGCCATGGCCCTCGAGGTGAAGCTGATGGARTC | 61 |
| MHyVH13 | GCTGCCCAACCAGCCATGGCCCTCGAGGTGCARCTTGTTGAGTC | 62 |
| MHyVH14 | GCTGCCCAACCAGCCATGGCCCTCGAGGTRAAGCTTCTCGAGTC | 63 |
| MHyVH15 | GCTGCCCAACCAGCCATGGCCCTCGAGGTGAARSTTGAGGAGTC | 64 |
| MHyVH16 | GCTGCCCAACCAGCCATGGCCCTCGAGGTTACTCTRAAAGWGTSTG | 65 |
| MHyVH17 | GCTGCCCAACCAGCCATGGCCCTCGAGGTCCAACTVCAGCARCC | 66 |
| MHyVH18 | GCTGCCCAACCAGCCATGGCCCTCGAGGTGAACTTGGAAGTGTC | 67 |
| MHyVH19 | GCTGCCCAACCAGCCATGGCCCTCGAGGTGAAGGTCATCGAGTC | 68 |
| Heavy chain (VH): reverse primer | | |
| MHylgGCH1-81 | CGATGGGCCCTTGGTGGAGGCTGAGGAGACGGTGACCGTGGT | 69 |
| MHylgGCH1-82 | CGATGGGCCCTTGGTGGAGGCTGAGGAGACTGTGAGAGTGGT | 70 |
| MHYlgGCH1-83 | CGATGGGCCCTTGGTGGAGGCTGCAGAGACAGTGACCAGAGT | 71 |
| MHYlgGCH1-84 | CGATGGGCCCTTGGTGGAGGCTGAGGAGACGGTGACTGAGGT | 72 |

As described above, specific embodiments of the present disclosure have been described in detail, and it is apparent to those of ordinary skill in the art that such a specific description is only a preferred embodiment, and the scope of the present disclosure is not limited thereby. Accordingly, it is intended that the substantial scope of the present disclosure be defined by the appended claims and equivalents thereof.

What is claimed is:

1. An antibody binding to Super-repressor IκB (srIκB) or an antigen-binding fragment thereof, the antibody or the antigen-binding fragment thereof comprising a heavy chain variable region (VH) and a light chain variable region (VL), wherein the VH comprises a heavy chain CDR1 of SEQ ID NO:3, a heavy chain CDR2 of SEQ ID NO:4, and a heavy chain CDR3 of SEQ ID NO:5; and the VL comprises a light chain CDR1 of SEQ ID NO: 6, a light chain CDR2 of SEQ ID NO:7, and a light chain CDR3 of SEQ ID NO:8.

2. The antibody binding to srIκB or antigen-binding fragment thereof of claim 1, wherein the VH comprises the amino acid sequence selected from the group consisting of the amino acid sequences of SEQ ID NOS: 9-14; and the VL comprises the amino acid sequence selected from the group consisting of the amino acid sequences of SEQ ID NOs: 15-29.

3. A composition comprising the antibody or antigen-binding fragment thereof of claim 1.

4. A nucleic acid encoding an antibody or an antigen-binding fragment thereof of following:

i) an antibody binding to srIκB or an antigen-binding fragment thereof, the antibody or the antigen-binding fragment thereof comprising a heavy chain variable region (VH) and a light chain variable region (VL), wherein the VH comprises a heavy chain CDR1 of SEQ ID NO:3, a heavy chain CDR2 of SEQ ID NO:4, and a heavy chain CDR3 of SEQ ID NO:5; and the VL comprises a light chain CDR1 of SEQ ID NO:6, a light chain CDR2 of SEQ ID NO:7, and a light chain CDR3 of SEQ ID NO: 8; or ii) an antibody binding to srIκB or an antigen-binding fragment thereof, the antibody or the antigen-binding fragment thereof comprising a heavy chain variable region (VH) and a light chain variable region (VL), wherein the VH comprises the amino acid sequence selected from the group consisting of the amino acid sequences of SEQ ID NOs: 9-14 and the VL comprises the amino acid sequence selected from the group consisting of the amino acid sequences of SEQ ID NOs: 15-29.

5. A vector comprising the nucleic acid of claim 4.

6. An isolated host cell into which the nucleic acid of claim 4 is introduced.

7. An isolated host cell into which the vector of claim 5 is introduced.

8. A method of preparing an antibody binding to srIκB or an antigen-binding fragment thereof, the method comprising:

(a) culturing the host cell of claim 7; and (b) collecting the antibody or the antigen-binding fragment thereof from the cultured cells of (a).

\* \* \* \* \*